US012693293B2

(12) United States Patent
Emam et al.

(10) Patent No.: US 12,693,293 B2
(45) Date of Patent: Jul. 28, 2026

(54) DEVICES AND METHODS FOR DETECTION OF VIRUSES FROM EXHALED BREATH

(71) Applicant: Northeastern University, Boston, MA (US)

(72) Inventors: Shadi Emam, Boston, MA (US); Nian-Xiang Sun, Winchester, MA (US)

(73) Assignee: Northeastern University, Boston, MA (US)

( * ) Notice: Subject to any disclaimer, the term of this patent is extended or adjusted under 35 U.S.C. 154(b) by 511 days.

(21) Appl. No.: 18/260,881

(22) PCT Filed: Jan. 26, 2022

(86) PCT No.: PCT/US2022/013850
§ 371 (c)(1),
(2) Date: Jul. 10, 2023

(87) PCT Pub. No.: WO2022/164863
PCT Pub. Date: Aug. 4, 2022

(65) Prior Publication Data

US 2024/0110914 A1 Apr. 4, 2024

Related U.S. Application Data

(60) Provisional application No. 63/143,763, filed on Jan. 29, 2021.

(51) Int. Cl.
*G01N 33/569* (2006.01)
*B01J 20/26* (2006.01)
(Continued)

(52) U.S. Cl.
CPC ...... *G01N 33/56983* (2013.01); *B01J 20/262* (2013.01); *B01J 20/268* (2013.01);
(Continued)

(58) Field of Classification Search
CPC .. B01J 20/262; B01J 20/268; B01J 20/28035; G01N 2333/165; G01N 27/126; G01N 33/5438; G01N 33/56983
See application file for complete search history.

(56) References Cited

U.S. PATENT DOCUMENTS

| | | | |
|---|---|---|---|
| 6,004,442 | A | 12/1999 | Choulga et al. |
| 11,219,387 | B2 | 1/2022 | Sun et al. |

(Continued)

FOREIGN PATENT DOCUMENTS

| | | | |
|---|---|---|---|
| KR | 10-2015-0006200 | A | 1/2015 |
| WO | 2010/025547 | A1 | 3/2010 |

(Continued)

OTHER PUBLICATIONS

Michaelson, D.M., (2014). "APOE epsilon4: the most prevalent yet understudied risk factor for Alzheimer's disease" Alzheimers Dement, 10(6): 861-868.

(Continued)

*Primary Examiner* — Jennifer Wecker
(74) *Attorney, Agent, or Firm* — Hamilton, Brook, Smith & Reynolds, P.C.

(57) ABSTRACT

Described herein is a sensor comprising a doped silicon layer, a graphene layer on the doped silicon layer, a molecularly imprinted polymer (MIP) layer on the graphene layer, and electrodes in operative arrangement with the MIP layer and configured to provide a signal indicative of resistance. The MIP layer is derived from a MIP monomer and functional monomer. Also described herein is a detector comprising a sensor described herein as well as methods of making and using the sensors and detectors, e.g., to detect an analyte, such as a virus.

21 Claims, 9 Drawing Sheets

(51) Int. Cl.
*B01J 20/28* (2006.01)
*G01N 27/12* (2006.01)
*G01N 33/543* (2006.01)

(52) U.S. Cl.
CPC ...... *B01J 20/28035* (2013.01); *G01N 27/126* (2013.01); *G01N 33/5438* (2013.01); *G01N 2333/165* (2013.01)

(56) References Cited

U.S. PATENT DOCUMENTS

| | | | |
|---|---|---|---|
| 11,701,031 B2 | 7/2023 | Sun | |
| 2016/0377611 A1 | 12/2016 | Ma et al. | |
| 2019/0313944 A1 | 10/2019 | Sun et al. | |
| 2020/0200694 A1 | 6/2020 | Agnihotra et al. | |
| 2021/0010968 A1* | 1/2021 | Piletsky | G01N 33/5438 |
| 2022/0167873 A1 | 6/2022 | Sun et al. | |
| 2022/0346679 A1* | 11/2022 | Kendall | B01J 20/226 |
| 2023/0296597 A1 | 9/2023 | Sun et al. | |

FOREIGN PATENT DOCUMENTS

| | | | |
|---|---|---|---|
| WO | 2013/022545 A1 | 2/2013 | |
| WO | WO-2021195626 A1 * | 9/2021 | B01J 20/268 |
| WO | 2021/231421 A1 | 11/2021 | |
| WO | 2022/035462 A1 | 2/2022 | |
| WO | 2022/164863 A1 | 8/2022 | |

OTHER PUBLICATIONS

Nakamura, A., et al., "High performance plasma amyloid-ß biomarkers for Alzheimer's disease", 2018, Nature 554: 249-273.
Nakhleh, M.K., et al., "Diagnosis and classification of 17 diseases from 1404 subjects via pattern analysis of exhaled molecules", ACS Nano 2017, 11, 112-125.
Non-Final Office Action for U.S. Appl. No. 16/383,220, "Molecularly-Imprinted Electrochemical Sensors" Dated May 4, 2021.
Notice of Allowance and Fees Due (PTOL-85) Mailed on Mar. 7, 2023 for U.S. Appl. No. 17/453,941, 9 page(s).
Notice of Allowance for U.S. Appl. No. 16/383,220, "Molecularly-Imprinted Electrochemical Sensors;" Dated Sep. 1, 2021.
Parisi, O. I., et al., "Monoclonal-type" plastic antibodies for SARS-CoV-2 based on Molecularly Imprinted Polymers, BioRxiv, May 28, 2020, 13 pages.
Park, S., et al., "Hydrazine-reduction of graphite- and graphene oxide" Carbon 2011, 49, 3019-3023.
Pauling, L., et al., "Quantitative analysis of urine vapor and breath by gas-liquid partition chromatography", Proc Natl Acad Sci, 68 (10):2374-6 (Oct. 1971).
PCT International Preliminary Report on Patentability and Written Opinion for International Application No. PCT/US2021/014248, mailed on Feb. 23, 2023.
PCT International Preliminary Report on Patentability and Written Opinion for International Application No. PCT/US2022/013850, entitled "Devices and Methods for Detection of Viruses from Exhaled Breath", Date of Mailing: Aug. 10, 2023.
PCT International Search Report and Written Opinion for International Application No. PCT/US2022/013850, entitled "Devices and Methods for Detection of Viruses from Exhaled Breath", Date of Mailing: Apr. 29, 2022.
PCT International Search Report and Written Opinion received for International Application No. PCT/US2021/014248, mailed on Apr. 28, 2021, 12 pages.
Pei, S., et al., "The reduction of graphene oxide", Carbon, 50 (2012) 3210-3228.
Peng, G., et al., "Detection of Nonpolar Molecules by Means of Carrier Scattering in Random Networks of Carbon Nanotubes: Toward Diagnosis of Diseases via Breath Samples", Nanoletters, 9(4): 1362-1368 (Jan. 2009).
Ping, A, et al., "An amperometric sensor based on Prussian blue and poly(o-phenylenediamine) modified glassy carbon electrode for the determination of hydrogen peroxide in beverages", Food Chem. 2011, 126, 2005-2009.
Prabakaran P, et al., "A model of the ACE2 structure and function as a SARS-CoV receptor", Biochem Biophys Res Commun. Jan. 30, 2004;314(1):235-41.
Rajesh, et al., "Single Frequency Impedance Analysis on Reduced Graphene Oxide Screen-Printed Electrode for Biomolecular Detection", Applied Biochemistry And Biotechnology, Humana Press Inc, New York, vol. 183, No. 2, May 22, 2017, p. 672-683.
Rebelo Tania SC R et al.: "Molecularly imprinted polymer SPE sensor for analysis of CA-125 on serum", Analytica Chimica Acta, Elsevier, Amsterdam, NL, vol. 1082, Jul. 26, 2019 (Jul. 26, 2019), pp. 126-135, XP085762495.
Saylan, Y., et al., "Molecular Imprinting of Macromolecules for Sensor Applications," Sensors, 2017, 17, 898.
Schedin, F., et al., "Detection of individual gas molecules adsorbed on graphene", Nat. Mater. 2007, 6, 652-655, doi:http://dx.doi.org/10.1038/nmat1967. 17660825.
Schmidt, F.M., et al., "Ammonia in breath and emitted from skin". J Breath Res. 2013, 7, 017109.
Selkoe, DJ., et al., "The role of APP processing and trafficking pathways in the formation of amyloid beta-protein", Ann. NY Acad. Sci. 1996, 777, 57-64.
Seo, G., et al., "Rapid Detection of COVID-19 Causative Virus (SARS-CoV-2) in Human Nasopharyngeal Swab Specimens Using Field-Effect Transistor-Based Biosensor", ACS Nano 2020 14 (4), 5135-5142.
Shang, J., et al., "Structural basis of receptor recognition by SARS-CoV-2", Nature 581, 221-224 (2020).
Sharma Sonika et al: "Surface Plasmon Resonance Based Highly Selective Fiber Optic Dopamine Sensor Fabricated Using Molecular Imprinted GNP/SnO2 Nanocompo site", Journal of Lightwave Technology, IEEE, USA, vol. 36, No. 24, Dec. 15, 2018 (Dec. 15, 2018), pp. 5956-5962, XP011702085.
Stankovich, S., et al., "Synthesis of graphene-based nanosheets via chemical reduction of exfoliated graphite oxide", Carbon 45 (2007) 1558-1565.
Supplemental Notice of Allowability for U.S. Appl. No. 16/383,220, "Molecularly-Imprinted Electrochemical Sensors", Dated Nov. 3, 2021.
Tisch, U., et al., "Detection of Alzheimer's and Parkinson's disease from exhaled breath using nanomaterial-based sensors", 2013, J Nanomedicine 8(1): 43-56.
Urraca, et al., "Polymeric complements to the Alzheimer's disease biomarker ß-amyloid isoforms AßI-40 and AßI-42 for blood serum analysis under denaturing conditions", Journal of the American chemical society 2011, I33, 9220-9223.
Van der Linden, W.E., et al., "Glassy carbon as electrode material in electro- analytical chemistry", Anal Chim Acta 1980; 119:1-24.
Vasapollo, G., et al., "Molecularly Imprinted Polymers: Present and Future Prospective", Int. J Mol. Sci. 2011, 12, 5908-5945.
Wyllie, AL., "Saliva is more sensitive for SARS-COV-2 detection in COVID-19 patients than nasopharyngeal swabs", medRxiv, Apr. 22, 2020, 12 pages, doi: https://doi.org/10. I 101/2020.04.16.20067835.
Yang Minghui et al., "Immunosensor for the detection of cancer biomarker based on percolated graphene thin film", Chemical Communications, vol. 46, No. 31, Jun. 28, 2010 (Jun. 28, 2010), p. 5796, XP055796852.
Zhang Xian et al: "Multifunctional oligomer immobilized on quartz crystal microbalance: a facile and stabilized molecular imprinting strategy for glycoprotein detection", Analytical and Bioanalytical Chemistry, Springer Berlin Heidelberg, DE, vol. 411, No. 17, May 22, 2019 (May 22, 2019) , pp. 3941-3949, XP036819481.
Zhang, M., et al., "Interlocked graphene-Prussian blue hybrid composites enable multifunctional electrochemical applications", Biosensors and Bioelectronics 2017, 89, 570-577.
Zhang, X., et al., "Characterization of the receptor-binding domain (RBD) of 2019 novel coronavirus: implication for development of RBD protein as a viral attachment inhibitor and vaccine", Cell Mol Immunol 17, 613-620 (2020).

(56) References Cited

OTHER PUBLICATIONS

Zhao, J. et al., "Graphene quantum dots-based platform for the fabrication of electrochemical biosensors", Electrochem. Commun. 2011, 13, 31-33.
Zhou, Heng et al. "Sensitive and selective voltammetric measurement of Hg2+ by rational covalent functionalization of graphene oxide with cysteamine", The Analyst 137, 305-8 (2012).
Chen, Y., Ren, R., Pu, H et al., Field-Effect Transistor Biosensor for Rapid Detection of Ebola Antigen. Scientific Reports 7, 10974 (2017). (Year: 2017).
Forssen et al., Advanced Analysis of Biosensor Data for SARS-CoV-2 RBD and ACE2 Interactions. Analytical Chemistry, vol. 92/Issue 17. (Year: 2020).
Kirchner et al., Recent developments in carbon-based two-dimensional materials: synthesis and modification aspects for electrochemical sensors. Microchimica Acta (2020) 187: 441. (Year: 2020).
Layqah et al., An electrochemical immunosensor for the corona virus associated with the Middle East respiratory syndrome using an array of gold nanoparticle-modified carbon electrodes. Microchimica Acta (2019) 186: 224 (Year: 2019).
Mavrikou et al., Development of a Portable, Ultra-Rapid and Ultra-Sensitive Cell-Based Biosensor for the Direct Detection of the SARS-CoV-2 S1 Spike Protein Antigen. Sensors 2020, 20(11), 3121. (Year: 2020).
Ogawa et al., The D614G mutation in the SARS-CoV2 Spike protein increases infectivity in an ACE2 receptor dependent manner. bioRxiv preprint doi: https://doi.org/10.1101/2020.07.21.214932; this version posted Jul. 22, 2020. (Year: 2020).
Omotuyi et al., Atomistic simulation reveals structural mechanisms underlying D614G spike glycoprotein-enhanced fitness in SARS-COV-2. J. Comput. Chem. 2020; 41:2158-2161. (Year: 2020).
Pohanka et al., Serological Diagnosis of Tularemia in Mice Using the Amperometric Immunosensor. Electroanalysis 19, 2007, No. 24, 2507-2512. (Year: 2007).
Skladal et al., Biosensors for Detection of Francisella Tularensis and Diagnosis of Tularemia. Biosensors, (Chapter 7 edited by Pier Andrea Serra, 2010, pp. 115-125, ISBN 978-953-7619-99-2).
Tan et al., A SARS-CoV-2 surrogate virus neutralization test based on antibody-mediated blockage of ACE2-spike protein-protein interaction. Nat. Biotechnol. Sep. 2020; 38(9): 1073-1078. doi: 10.1038/s41587-020-0631-z. Epub Jul. 23, 2020. PMID: 32704169. (Year: 2020).
Zhao et al., Enzyme-based Electrochemical Biosensors. Biosensors, Chapter 1, edited by Pier Andrea Serra, 2010, pp. 1-22, ISBN 978-953-7619-99-2).
Zhou et al., A pneumonia outbreak associated with a new coronavirus of probable bat origin. Nature, 579, Mar. 12, 2020, pp. 270-289. (Year: 2020).
2018 Alzheimer's disease facts and figures, Alzheimer's association, (2018), 1-88.
Algieri, C., et al., "Bio-Mimetic Sensors Based on Molecularly Imprinted Membranes", Sensors, 2014, 14 13863-13912.
Alizadeh, T. et al., "Graphene/graphite/molecularly imprinted polymer nanocomposite as the highly selective gas sensor for nitrobenzene vapor recognition", Journal of Environmental Chemical Engineering 2014, 2, 1514-1526.
Alzheimer's Association, 2016 Alzheimer's disease facts and figures, Alzheimer's & Dementia 2016, 12, 459-509.
Bach, J., et al., "Measuring Compounds in Exhaled Air to Detect Alzheimer's Disease and Parkinson's Disease", PLOS One, 13 pgs, (Jul. 13, 2015).
Bredesen, D.E., et al., "Reversal of cognitive decline: A novel therapeutic program", Aging 6(9): 707-717 (Sep. 2014).
Broza, Y., et al., "Nanomaterial-based sensors for detection of disease by volatile organic compounds", Nanomedicine (2013) 8(5): 785-806.
Buszewski, B., et al., "Human exhaled air analytics: biomarkers of diseases", Biomedical Chromatography, 21: 553-566 (2007).
Cai, et al., "Distinct conformational states of SARS-CoV2 spike protein," Science 369, 10.1126/science.abd4251 (2020).
Canter, R. G., et al., "The road to restoring neutral circuits for the treatment of Alzheimer's disease", Nature 2016, 539.
Capuano, R., et al., "The lung cancer breath signature: a comparative analysis of exhaled breath and air sampled from inside the lungs", Scientific Reports, 5:16491, 10 pages (2015).
Chatterjee, T.N., et al., "A Molecularly Imprinted Polymer-Based Technology for Rapid Testing of COVID-19", Transactions of the Indian National Academy of Engineering (2020): 5: 225-228.
Chen, X., et al., "A study of an electronic nose for detection of lung cancer based on a virtual SAW gas sensors array and imaging recognition method", Meas. Sci. Technol. 16 (2005) 1535-1546.
Chen, X., et al., "Molecular imprinting: perspectives and applications" Chem. Soc. Rev., 2016, 45, 2137.
Clyde, D. Dean., Svec, H.J., "Vapor pressures of some amino acids", Ames Laboratory., U.S. Atomic Energy Commission, Nov. 1963, 41 pages.
Cui, M., et al., "A Molecularly-Imprinted Electrochemical Sensor Based on a Graphene-Prussian blue Composite-Modified Glassy Carbon Electrode for the Detection of Butylated Hydroxyanisole in Foodstuffs", 2013, J. Analyst 138: 5949-5955.
De Meyer, G., et al., "Diagnosis-Independent Alzheimer Disease Biomarker Signature in Cognitively Normal Elderly People", Arc Neurol, 67(8): 949-956 (Aug. 2010).
Dekansi, A, et al., "Glassy carbon electrodes Characterization and electrochemical activation", Carbon 39 (2001) 1195-1205.
Dent, A.G., et al., "Exhaled breath analysis for lung cancer", J. Thorac Dis 2013; 5(S5): S540-S550.
Dickert, F.L., et al., "Synthetic receptors for chemical sensors-subnano- and micrometer patterning by imprinting techniques", J of Biosensors and Bioelectronics, 2004, 20(6), 1040-1044.
Dumurgier, J., et al., "Alzheimer's Biomarkers and Future Decline in Cognitive Normal Older Adults", J. Alzheimers Dis. 2017; 60(4): 1451-1459.
Emam, S., et al., "A Molecularly-Imprinted Electrochemical Gas Sensor to Detect Pivalic Acid in the Air," RISE:2018 Research, Innovation & Scholarship Expo, Northeastern University, Apr. 5, 2018.
Emam, S., et al., "A Molecularly-Imprinted Electrochemical Gas Sensor to Sense Butylated Hydroxytoluene in Air", 2018, J of Sensors 2018: 1-9.
Emam, S., et al., "Electrochemical Gas Sensor to Diagnose Alzheimer's Disease Through Exhaled Breath," RISE:2017 Research, Innovation & Scholarship Expo, Northeastern University, Apr. 13, 2017.
Ertürk, G., et al., "Molecular imprinting techniques used for the preparation of biosensors", Sensors, 2017, 17, 288.
Gan, et al: "Electrochemical sensors based on graphene materials", Microchimica Acta; An International Journal On Micro And Traceanalysis, Springer-Verlag, VI, vol. 175, No. 1-2, Jul. 7, 2011.
Gunther, E.C., et al., "Rescue of Transgenic Alzheimer's Pathophysiology by Polymeric Cellular Prion Protein Antagonists", Cell Reports 26, 145-158, Jan. 2, 2019.
Hibbard, T., et al., Breath ammonia analysis: Clinical application and measurement. Breath Ammon. Clin. App. Meas. 2011, 41, 21-35.
Hu, W.T., et al., "Biomarker Discovery of Alzheimer's Disease, Frontotemporal Lobar Degeneration and Parkinson's Disease", Acta Neuropathol. Sep. 2010; 120(3): 385-399.
Huang, Y., et al. "Structural and functional properties of SARS-CoV-2 spike protein: potential antivirus drug development for COVID-19", Acta Pharmacol Sin 41, 1141-1149 (2020).
Hummers W. S., et al., "Preparation of graphene oxide", J. Am. Chem. Soc. 1958, 80, 1339.
Hwang, EH., et al., "Transport in chemically doped graphene in the presence of adsorbed molecules". Phys. Rev. B 76:195-421 (Oct. 30, 2018).
Taccarino F.H et al., "Gamma frequency entrainment attenuates amyloid load and modifies microglia" Nature 2016, 540, 230-252.
Ibrahim IM, et al., "COVID-19 spike-host cell receptor GRP78 binding site prediction", J Infect. May 2020; 80(5):554-562.
Janiak, D.S., et al., "Molecular imprinting of peptides and proteins in aqueous media", Anal Bioanal Chem 2007, 389, 399-404.

(56) References Cited

OTHER PUBLICATIONS

Jin, E., et al., "Fabrication of graphene/prussian blue composite nanosheets and their electrocatalytic reduction ofH2O2", Electrochimica Acta 2010, 55, 7230-7234.
Katsnelson, M.I., et al., "Graphene: new bridge between condensed matter physics and quantum electrodynamic," (2007) J of Solid State Commun. 143: 3-13.
Kleisiaris, C.F., et al., "Health care practices in ancient Greece: The Hippocratic ideal", J Med Ethics Hist Med, 7 (6): 1-5 (2014).
Kong, Yu, "Molecular dynamics simulations of molecularly imprinted polymer approaches to the preparation of selective materials to remove norfloxacin," J. Appl. Polym. Sci., (2016), 42817, 11 pages.
Lan, J., et al., "Structure of the SARS-CoV-2 spike receptor-binding domain bound to the ACE2 receptor", Nature 581, 215-220 (2020).
Leung, N.H.L., et al., "Respiratory virus shedding in exhaled breath and efficacy of face masks", Nat Med 26, 676-680 (2020).
Li, J, et al., "Prussian Blue/Reduced Graphene Oxide Composite for the Amperometric Determination of Dopamine and Hydrogen Peroxide", Analytical Letters 2015, 48:17, 2786-2798, DOI: 10.1080/00032719.2015.1052141.
Li, X., et al., "Highly sensitive protein molecularly imprinted electro-chemical sensor based on bold microdendrites electrode and Prussian blue mediated amplification", Biosensors and Bioelectronics 42 (2013): 612-617.
Liguoril, C., et al., "Beta-amyloid and phosphorylated tau metabolism changes in narcolepsy over time", Sleep Breath 2016, 20, 277-283.
Lin, CY., et al., "Discrimination of Peptides by Using a Molecularly Imprinted Piezoelectric Biosensor" Chem. Eur. J. 2003, 9: 5107-5110.
Liu, Fangze, "Quantum Carrier Reinvestment-Induced Ultrahigh and Broadband Photocurrent Responses in Graphene-Silicon Junctions," ACS Nano, vol. 8, No. 10, p. 10270-10279 (Oct. 3, 2014).
Luo, Jing, "Electrochemical sensor for bovine hemoglobin based on a novel graphene-molecular imprinted polymers composite as recognition element," Sensors and Actuators B 203, (2014) , p. 782-789.
Mao, Yan, "Electrochemical sensor for dopamine based on a novel graphene-molecular imprinted polymers composite recognition element," Biosensors and Bioelectronics, (Jul. 28, 2011), p. 291-297.
Mazzatenta, A, et al., "Volatile organic compounds (VOCs) fingerprint of Alzheimer's disease", Respiratory Physiology & Neurobiology 2015, 209, 81-84.
McKhann, G.M., et al., "The diagnosis of dementia due to Alzheimer's disease: recommendations from the National Institute on Aging-Alzheimer's Association workgroups on diagnostic guidelines for Alzheimer's disease", Alzheimer's & Dementia, 7 (2011) 263-269.
Adams, et al., "A Molecularly Imprinted Polymer-Graphene Sensor Antenna Hybrid for Ultra Sensitive Chemical Detection," IEEE Sensors Journal, vol. 19, No. 16, Aug. 15, 2019.

* cited by examiner

DEVICES AND METHODS FOR DETECTION OF VIRUSES FROM EXHALED BREATH

RELATED APPLICATION

This application is the U.S. National Stage of International Application No. PCT/US2022/013850, filed on Jan. 26, 2022, which designates the U.S., published in English, and claims the benefit of U.S. Provisional Application No. 63/143,763, filed on Jan. 29, 2021. The entire teachings of these applications are incorporated herein by reference.

GOVERNMENT SUPPORT

This invention was made with government support under grant number 2031142 awarded by the National Science Foundation. The government has certain rights in the invention.

BACKGROUND

In the last twenty years, several viral epidemics, such as the severe acute respiratory syndrome coronavirus (SARS-CoV) in 2002 to 2003, the H1N1 influenza in 2009, and the Middle East respiratory syndrome coronavirus (MERS-CoV) in Saudi Arabia in 2012, have been identified. Severe acute respiratory syndrome coronavirus 2 (SARS-CoV-2) is a new virus that causes COVID-19, which has killed hundreds of thousands of people so far. The respiratory symptoms of COVID-19 typically appear an average of 5-6 days after exposure but may appear in as few as 2 days or as many as 14 days after exposure, according to the U.S. Centers for Disease Control and Prevention (CDC). During all these times, the disease is transmissible.

Health officials first believed that the virus SARS-CoV-2 is transmitted only through droplets that are coughed or sneezed out, either directly or onto objects. But some scientists say there is preliminary evidence that airborne transmission in which the disease spreads in the much smaller particles from exhaled air, known as aerosols, is occurring. Compared with droplets, which are heftier and thought to travel only short distances after someone coughs or sneezes before falling to the floor or onto other surfaces, aerosols can linger in the air for longer and travel further. Aerosols are more likely to be produced by talking and breathing.

Routine confirmation of cases of COVID-19 is based on detection of unique sequences of virus RNA by nucleic acid amplification tests (NAAT), such as real-time reverse-transcription polymerase chain reaction (rRT-PCR), with confirmation by nucleic acid sequencing when necessary.

There exists a need for integrated, random-access, point-of-care devices that can provide for accurate diagnosis of SARS-CoV-2 infections.

SUMMARY

Provided herein is a sensor comprising a doped silicon layer, a graphene layer on the doped silicon layer, a molecularly imprinted polymer (MIP) layer on the graphene layer, and electrodes in operative arrangement with the MIP layer and configured to provide a signal indicative of resistance. The MIP layer is derived from a MIP monomer and functional monomer.

Also provided herein is a sensor comprising a doped silicon layer having an etched surface, a graphene layer on the etched surface, a MIP layer of poly(pyrrole-co-EGDMA-co-methacrylic acid) or poly(pyrrole-co-dopamine) on the graphene layer and electrodes in operative arrangement with the MIP layer and configured to provide a signal indicative of a resistance. The graphene layer comprises graphene and potassium ferrocyanide.

Also provided herein is a detector comprising a sensor described herein and a voltage source configured to apply a voltage to the MIP layer.

Also provided herein is a method of detecting an analyte in a sample. The method comprises measuring the resistance of a sensor described herein that is in contact with the sample to obtain a measured resistance. The sensor is selective for the analyte, and the measured resistance is indicative of presence or absence of the analyte in the sample.

Also provided herein is a method of detecting a viral infection in a subject. The method comprises measuring the resistance of a sensor described herein that is in contact with a sample from the subject to obtain a measured resistance. The sensor is selective for an analyte associated with the viral infection, and the measured resistance is indicative of presence or absence of the viral infection in the subject.

Also provided herein is a method of fabricating a sensor. The method comprises forming a graphene layer on a doped silicon layer, and forming a MIP layer derived from a MIP monomer and functional monomer on the graphene layer.

Compared to previous generations of electrochemical gas sensors, the third-generation sensor embodiments disclosed herein are much more selective, accurate, and consistent. In addition, the process for manufacturing the third-generation sensors is repeatable, and has been used to make 20 of these sensors, which are inexpensive, fast, non-invasive, and provide for accurate detection of COVID-19. In fact, the performance (e.g., accuracy) of these sensors is equivalent to the accuracy of RT-PCR, but is less expensive and much faster, for example, instant. Embodiments may be used for COVID-19 tests, for example, rapid COVID-19 tests, such as at hospitals, airports, schools, etc. Embodiments thus provide an instant COVID-19 diagnosis test and/or volatile organic compound (VOC) detection.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

Figure 1A:
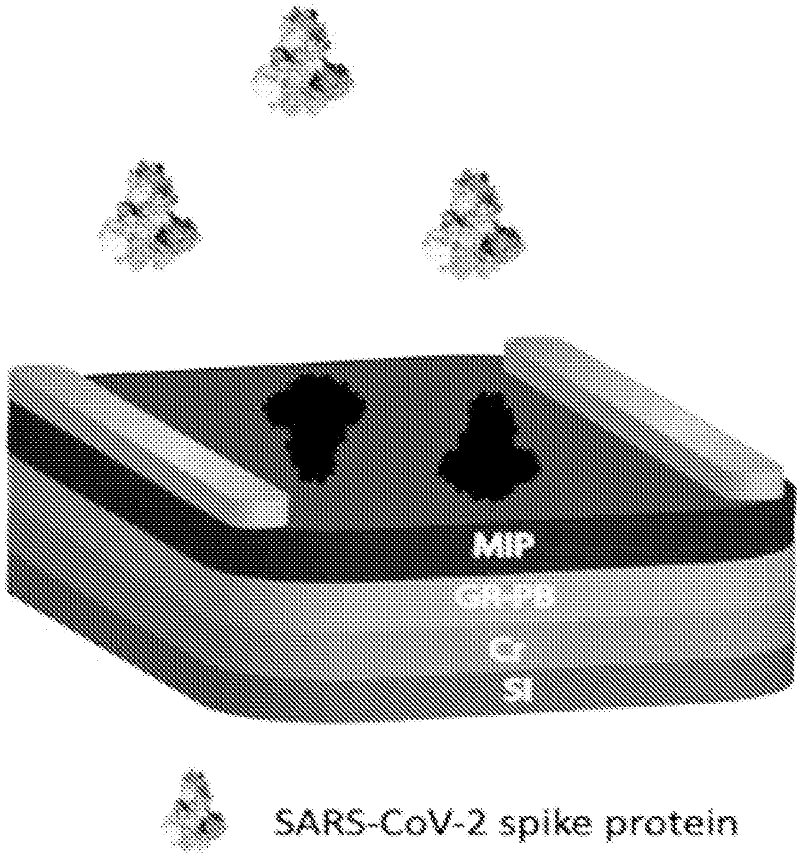
FIG. 1A is a depiction of a first-generation sensor, and shows a sensor fabricated by placing a template molecule (e.g., SARS-CoV-2 spike protein) inside a polymer matrix, and removing the template molecule after polymerization. The resulting cavity is about the size of the template molecule, but not the exact size.

A description of example embodiments follows.

Disclosed herein are embodiments of a sensor that can detect SARS-CoV-2 in the air (from exhaled breath, saliva, etc.). These sensors can be used at a point of care because they are capable of detecting virus in about 10 seconds. The embodiments of the sensors can be used in hospitals, airports, etc. The embodiments are third generation sensors to detect SARS-CoV-2 and are much more accurate, consistent, and selective compared to the previous generations.

The third generation of the electrochemical gas sensors to detect SARS-CoV-2 in the air were fabricated and tested. Example advantages of the third-generation sensors compared to the previous generation are improved consistency, repeatability, and selectivity. All the sensors were tested against bovine serum albumin (BSA), water, phosphate buffer solution (PBS), the Middle East respiratory syndrome (MERS), severe acute respiratory syndrome (SARS), Ebola, and flu virus. The new generation of sensors is highly selective, including as compared to the previous generations. First- and third-generation sensors were blind tested with an 86-sample kit. The first-generation sensor was 37.5% selective and 61% sensitive against the kit, while the third-generation sensor was 75% selective and 80% sensitive against the kit.

Sensors and Detectors

As used herein, the singular forms "a," "an" and "the" include plural referents unless the context clearly dictates otherwise. Thus, for example, reference to "a monomer" can include a plurality of monomers. Further, the plurality can comprise more than one of the same monomer, or a plurality of different monomers.

"About" means within an acceptable error range for the particular value, as determined by one of ordinary skill in the art. Typically, an acceptable error range for a particular value depends, at least in part, on how the value is measured or determined, e.g., the limitations of the measurement system. For example, "about" can mean within an acceptable standard deviation, per the practice in the art. Alternatively, "about" can mean a range of ±20%, e.g., ±10%, ±5% or ±1%, of a given value.

Provided herein in one embodiment is a sensor comprising a silicon layer (e.g., doped silicon layer), a graphene layer on the silicon layer (e.g., doped silicon layer), a molecularly imprinted polymer (MIP) layer on the graphene layer, and electrodes in operative arrangement with the MIP layer and configured to provide a signal indicative of resistance. In some aspects, the MIP layer is derived from a MIP monomer and functional monomer. In some aspects, the MIP layer is derived from a MIP monomer, cross-linking monomer and functional monomer. In some aspects, the MIP layer is derived from a MIP monomer and cross-linking monomer.

Silicon substrates, such as silicon wafers, typically form a layer of silicon dioxide upon exposure to air, or come with a layer of silicon dioxide grown thereon, e.g., using one of a variety of oxidation processes known in the art (e.g., wet or dry oxidation). In some aspects herein, the silicon layer has an etched surface. When a silicon layer (e.g., doped silicon layer) is described herein as having an "etched" surface, the silicon layer has a surface that lacks or substantially lacks a layer of silicon dioxide. Silicon dioxide can be removed from the surface of a layer of silicon using hydrofluoric acid, as described herein. Typically, only one surface (e.g., top surface, bottom surface) of a silicon layer (e.g., doped silicon layer) is etched, but both surfaces (e.g., top surface and bottom surface) of a silicon layer (e.g., doped silicon layer) can be etched. In some aspects, when a silicon layer (e.g., doped silicon layer) has an etched surface (e.g., etched top surface), the graphene layer is on the etched surface, as depicted, for example, in FIG. 1C.

Silicon doping is introducing impurities into silicon, typically for the purpose of modulating its properties. Doped silicon is preferred herein for its electrical properties, in particular, its lower resistance. Accordingly, in preferred aspects, a silicon layer is a doped silicon layer. In further aspects, doped silicon is highly doped. As used herein, "highly doped silicon" refers to silicon having a doping level of greater than 10^20 m^−3.

In some aspects, a silicon layer is from about 1 nanometer to about 1 micron, from about 1 nanometer to about 500 nanometers, from about 1 nanometer to about 100 nanometers, from about 1 nanometer to about 50 nanometers or from about 1 nanometer to about 10 nanometers thick. In a particular aspect, a silicon layer is about 5 nanometers thick.

It was found that removing chromium from the structure of the sensor improved adhesion of the graphene layer to the silicon layer and decreased a Schottky barrier height that forms in a metal-semiconductor junction. Accordingly, in the sensors described herein, the graphene layer is on the silicon layer (e.g., doped silicon layer).

As used herein, "graphene" refers to a single-layer sheet of $sp^2$-bonded carbon atoms arranged in a hexagonal, honeycomb lattice. Graphene typically contains defects, such as oxygen- or nitrogen-centered defects. "Graphene" is meant to encompass these species as well. Thus, as used herein, "graphene" includes graphene oxide (GO) and reduced graphene oxide (rGO, GR).

"Graphene oxide" or "GO" is graphene modified with oxygen-containing functional groups such as epoxides, carbonyls, carboxyls and alcohols. Typically, the carbon to oxygen ratio of graphene oxide is about three to about one. In some aspects, graphene is graphene oxide.

"Reduced graphene oxide," "rGO" or "GR" is the product resulting from the reduction of graphene oxide. Reduced graphene oxide can be produced by a number of techniques known in the art, including the so-called Hummer method, wherein a solution of graphene oxide is exposed to hydrazine hydrate, and the solution is maintained at about 100° C. for about 24 hours. In some aspects, graphene is reduced graphene oxide.

In some aspects, a graphene layer comprises graphene (e.g., reduced graphene oxide) and potassium ferrocyanide (also known as Prussian blue). Methods of making graphene comprising potassium ferrocyanide are known in the art and described in the Exemplification herein.

In some aspects, a graphene layer comprises one or more layers of graphene, for example, from about one to about 500, from about one to about 50, from about one to about 25, or from about 5 to about 15 layers of graphene. For example, in some aspects, a graphene layer comprises 1, 2, 3, 4, 5, 6, 7, 8, 10, 15, about 15, 20, about 20, 25, about 25, 50, about 50, 75, about 75, 100, about 100, 150, about 150, 200, about 200, 250, about 250, 300, about 300, 350, about 350, 400, about 400, 450, about 450, 500 or about 500 layers of graphene. In a particular aspect, a graphene layer comprises from about 5 to about 10 layers of graphene.

As used herein, "molecularly imprinted polymer," or "MIP," refers to a polymer created using molecular imprinting technology. Typically, in molecular imprinting technology, a template molecule is placed in solution with a polymerizable monomer, or "MW monomer." Polymerization is initiated, e.g., upon application of voltage. After polymerization, a washing agent can be used to remove the template molecule, and to reveal cavities that trap the same size and shape of molecule as the template molecule. The polymeric matrix of a "molecularly imprinted polymer" is characterized by molecular recognition sites specific to one or more analytes that enable the MW to selectively bind the one or more analytes. Molecular imprinting technologies for creating MIPs are well-known in the art, and described in the Exemplification herein, as well as in Saylan, Y., et al., "Molecular Imprinting of Macromolecules for Sensor Applications," *Sensors,* 2017, 17, 898; Erturk, G. and Mattiasson, B., "Molecular Imprinting Techniques Used for the Preparation of Biosensors," *Sensors* 2017, 17, 288; and Chen, L., et al., "Molecular imprinting: perspectives and applications," *Chem. Soc. Rev.,* 2016, 45, 2137, the relevant teachings of which are incorporated herein by reference in their entireties.

Selection of appropriate template molecules is within the skill of a person skilled in the art, and described herein. In some aspects, a template molecule is the analyte as, for example, is often the case for molecularly imprinted polymers for volatile organic compound detection. In some aspects, a template molecule is a portion of the analyte as, for example, is more common for larger analytes, such as peptides, carbohydrates, proteins and viruses. In some aspects, the template molecule is a receptor-binding domain of a virus (e.g., SARS1, SARS2, SARS-CoV-2, flu or Ebola virus). In some aspects, the template molecule is a glycoprotein, such as a glycosylated spike protein. In a particular aspect, the template molecule is the receptor binding domain of the glycosylated spike protein of SARS-CoV-2. Cai et al., *Science* 369, 1586-1592 (2020), the entire content of which is incorporated by reference herein, disclose protein sequences for the spike protein of SARS-CoV-2 and the receptor binding domain of the spike protein of SARS-CoV-2. Spike protein of SARS-CoV-2 and receptor binding domain of the spike protein of SARS-CoV-2 consistent with those disclosed in Cai et al. were used as template molecules in the examples described herein.

In some aspects, the template molecule has a molecular weight of less than about 500,000 daltons, for example, less than about 250,000 daltons, less than about 150,000 daltons, less than about 100,000 daltons, less than about 50,000 daltons. In some aspects, the template molecule has a molecular weight of about 35,000 daltons.

It will be understood that molecularly imprinted polymers, like polymers generally, are composed substantially or entirely of repeated monomeric subunits. Polymers can, therefore, be said to be derived from the monomer(s) that make up the repeated monomeric subunits. For example, polypyrrole can be described as being derived from pyrrole. Examples of MIP monomers from which a molecularly imprinted polymer can be derived include acrylic acid, methacrylic acid, 2-(trifluoromethly)acrylic acid, itaconic acid, p-vinylbenzoic acid, 2-acrylamido-2-methyl-1propansulfonic acid, divinylbenzene, 4-vinylbenzene boronic acid, 2-vinylpyridine, 4-vinylpyridine, N,N-diethylaminoethylmethacrylate, 1-vinylimidazole, allylamine, 4-(5-vinylimidazole), N-(2-aminoethyl)methacrylamide, N,N'-diethyl-4-styrylamidine, N,N,N-trimethylaminoethylmethacrylate, N-vinylpyrrolidone, urocanic ethyl ester, pyrrole, methyl methacrylate, 2-hydroxyethylmethacrylate, 4-ethyl styrene, acrylamide, methacrylamide, trans-3-(3-pyridyl)-acrylic acid, acrylonitrile and styrene, and any combination of the foregoing. In some aspects, the MW monomer is acrylic acid, methacrylic acid, 2-(trifluoromethly)acrylic acid, itaconic acid, p-vinylbenzoic acid, 2-acrylamido-2-methyl-1propansulfonic acid, divinylbenzene, 4-vinylbenzene boronic acid, 2-vinylpyridine, 4-vinylpyridine, N,N-diethyl aminoethylmethacrylate, 1-vinylimidazole, allylamine, 4-(5-vinylimidazole), N-(2-aminoethyl)methacrylamide, N,N'-diethyl-4-styrylamidine, N,N,N-trimethylaminoethylmethacrylate, N-vinylpyrrolidone, urocanic ethyl ester, pyrrole, methyl methacrylate, 2-hydroxyethylmethacrylate, 4-ethyl styrene, acrylamide, methacrylamide, trans-3-(3-pyridyl)-acrylic acid, acrylonitrile or styrene, or a combination of any of the foregoing. In a particular aspect, the MW monomer is pyrrole.

One or more functional monomers can be included in a molecularly imprinted polymer to improve selectivity of the molecularly imprinted polymer. Without wishing to be bound by any particular theory, it is believed that functional monomers improve selectivity of molecularly imprinted polymers due to formation of a complex between the template molecule and functional monomer induced during a pre-polymerization step in the creation of the molecularly imprinted polymer. Upon removal of template molecule following polymerization of the molecularly imprinted polymer, the functional monomers are believed to act as blocks around the molecular recognition sites, assisting in detection of the target analyte. Thus, in some aspects, a MIP is further derived from a functional monomer.

"Functional monomer," as used herein, refers to a polymerizable monomer able to establish a covalent or non-covalent interaction with a template molecule and/or analyte. Examples of functional monomers include methacrylic acid, acrylamide, vinyl esters (e.g., 2-hydroxyethylacrylate, 2-hydroxyethylmethacrylate), dopamine, amino acids, and coumarin, or a salt of any of the foregoing. Other functional monomers include anthranilic acid, pyrrole, o-phenylenediamine, aniline, o-aminophenol, p-aminobenzoic acid, β-cyclodextrin, 2-mercaptobenzimidazole, 3-thiophene acetic acid, 3-acrylamidophenylboronic acid, m-aminophenylboronic acid, scopoletin, nicotinamide, dopamine, gallic acid, p-aminothiophenol, o-aminothiophenol, p-aminobenzene sulfonic acid, 5-amino-8-hydroxyquinoline, 2-amino-5-mercapto-1,3,4-thiadiazole, indole-3-acetic acid, catechol, eriochrome black T, 3-thienylboronic acid, melamine, methylene green, 3,4-ethylenedioxythiophene, protoporphyrin IX, phenol, 3,4-propylenedioxythiophene, pyrrole derivatives, bithiophene, and bis(bithiophene) derivatives, or salt of any of the foregoing. Yet other examples of functional monomers include the functional monomers depicted in Scheme 1, or a salt thereof.

In some aspects, a functional monomer is methacrylic acid or dopamine, or a salt thereof, or a combination of any of the foregoing.

Scheme 1.

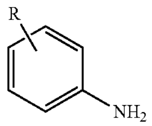

aniline

R = 2-OH: o-aminophenol

R = 2-$NH_2$: o-phenylenediamine

R = 2-SH: o-aminothiophenol

R = 3-OH: m-aminophenol

R = 3-$B(OH)_2$: (m-aminophenyl)boronic acid

R = 4-$SO_3H$: p-aminobenzene sulfonic acid

R = 4-SH: p-amincchiophenol

R = 4-$CO_2H$: p-aminobenzoic acid

pyrrole

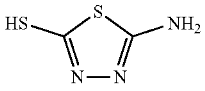

2-amino-S-mercapto-1,3,4-thiadiazole

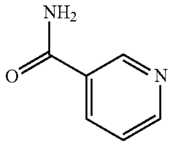

nicotinamide

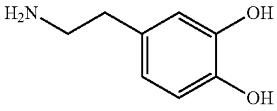

dopamine

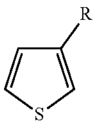

thiophene

R = $CH_2COOH$: 3-thiophene acetic acid

R = $B(OH)_2$: 3-thienylboronic acid

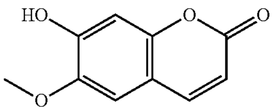

scopoletin

-continued
| Scheme 1. |
| --- |
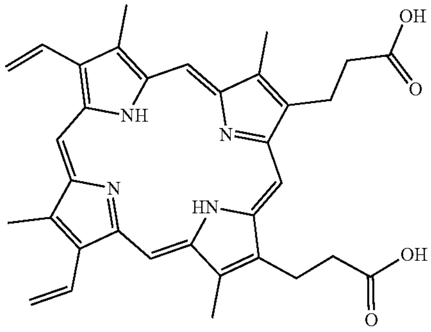
protoporphyrin ix
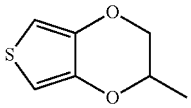
3,4-propylenedioxythiophene
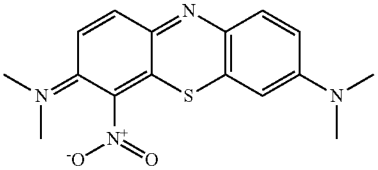
methylene green
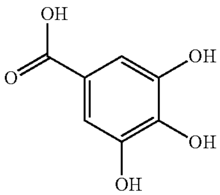
gallic acid
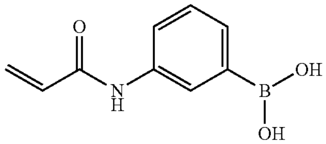
3-acrylamidophenylboronic acid
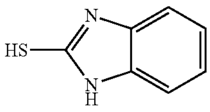
2-mercaptobenzimidazole -continued Scheme 1.

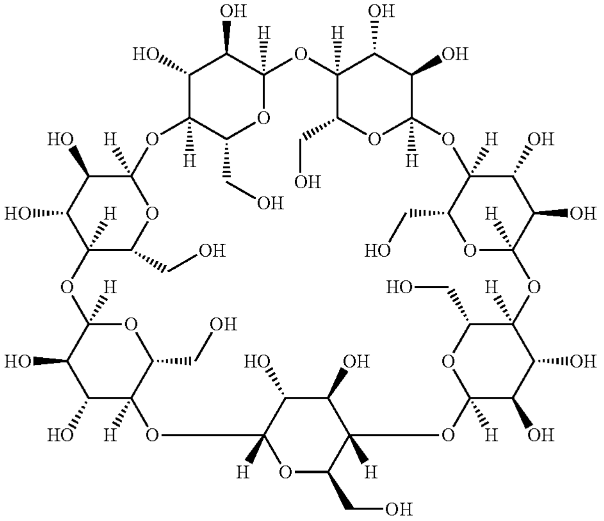

β-cyclodextrin

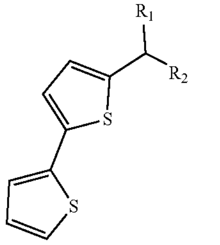

3,3'-(ethane-1,1-diyl)di-2,2'-bithiophene
when $R_2$ = biothiophene and;
$R_1$ = H: bis (2,2'-bithienyl)urethane
$R_1$ = 4-carboxyphenyl: bis(2,2'-bithienyl)-(4'-carboxyphenyl)methane
$R_1$ = benzo-18-crown-6: bis(2,2'-bithienyl)-benzo-[18-crown-6]methane
$R_1$ = 5,5-dimethyl-2-phenyl-1,3,2-dioxaborinane: bis(2,2'-bithienyl)-5,5-dimethyl-2-phenyl-(1,3,2)dioxaborinanemethane
when $R_1$ = O and $R_2$ = OH: 2,2'-bithiophene-5-carboxylic acid

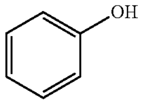

phenol

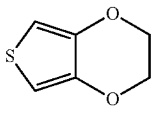

3,4-ethylenedioxythiophene

One or more cross-linking monomers can also or alternatively be included in a molecularly imprinted polymer. Without wishing to be bound by any particular theory, it is believed that cross-linking monomers link one polymer chain to another in the form of covalent bonds. Thus, in some aspects, a MIP is further derived from a cross-linking monomer. In some aspects, the cross-linking monomer is ethylene glycol dimethacrylate (EGDMA).

It will be appreciated that when a molecularly imprinted polymer is derived from functional monomers and/or cross-linking monomers in addition to MIP monomers, the resulting molecularly imprinted polymer is a co-polymer and, therefore, can be also be described by nomenclature used to describe co-polymers. For example, a molecularly imprinted polymer derived from a MIP monomer, cross-linking monomer and functional monomer, wherein the MIP monomer is pyrrole, the cross-linking monomer is EGDMA and the functional monomer is methacrylic acid can be referred to as poly(pyrrole-co-EGDMA-co-methacrylic acid), and can be used to form a MIP layer of poly(pyrrole-co-EGDMA-comethacrylic acid). A molecularly imprinted polymer derived from a MIP monomer and functional monomer, wherein the MIP monomer is pyrrole and the functional monomer is dopamine can be referred to as poly(pyrrole-co-dopamine), and can be used to form a MIP layer of poly(pyrrole-co-dopamine).

Also provided herein in an embodiment is a sensor comprising a doped silicon layer having an etched surface, a graphene layer on the etched surface, a MIP layer of poly(pyrrole-co-EGDMA-co-methacrylic acid) or poly(pyrrole-co-dopamine) on the graphene layer and electrodes in operative arrangement with the MIP layer and configured to provide a signal indicative of a resistance. The graphene layer comprises graphene and potassium ferrocyanide.

It will be understood that, though a sensor described herein may be described as being selective for an analyte, the selectivity of the sensor is mediated or substantially mediated by the MIP layer of the device. As used herein, a MIP layer or sensor described herein including a MIP "selectively binds" or "is selective for" an analyte if the MW binds to the analyte to a greater extent than at least one other, different analyte. In some aspects, the MW binds to its one or more cognate analytes at least two-fold, at least five-fold, at least ten-fold, or at least fifty-fold more strongly than the at least one other, different analyte. In some aspects, the MIP does not bind to the at least one other, different analyte to any measurable degree.

As described above, a MIP layer or sensor described herein including a MIP layer is selective for one or more analytes (e.g., 1, 2, 3, 4, 5, 6, 7, 8, 9, 10, etc.). In some aspects, the MIP layer or sensor including the MIP layer is selective for one analyte (e.g. a particular viral mutant, such as the delta and/or omicron mutant of SARS-COV-2). In some aspects, the MIP layer or sensor including the MIP layer is selective for more than one analyte (e.g., wild-type SARS-CoV-2, as well as delta and omicron mutants of SARS-CoV-2), as in an array. For example, the MIP layer or sensor including the MIP layer is selective for a set or subset of analytes associated with a particular disease or disorder.

Typically, the one or more analytes will be in fluid (i.e., liquid or gas) form. In some aspects, the one or more analytes are in gas form. In some aspects, the one or more analytes are in liquid (e.g., aerosol) form. In some aspects, the one or more analytes are in gas or aerosol form.

In some aspects, the one or more analytes are each a volatile organic compound. As used herein, "volatile organic compound" refers to any organic compound having a boiling point less than or equal to 250° C. measured at an atmospheric pressure of 101.3 kPa. Common examples of volatile organic compounds include, but are not limited to, acetone, acetic acid, butanal, carbon disulfide, ethanol, isopropyl alcohol, formaldehyde and methylene chloride. The United States Environmental Protection Agency also maintains a list of volatile organic compounds, which can be accessed at https://iaspub.epa.gov/sor_internet/registry/substreg/searchandretrieve/advancedsearch/search.do?details=displayDetails&selectedSubstanceId=83723.

MIPs selective for compounds up to about 3,000 daltons are routinely prepared. In some aspects, the one or more analytes has a molecular weight of less than about 3,000 daltons, less than about 1,000 daltons or less than about 500 daltons.

MIPs selective for larger analytes, such as peptides, carbohydrates, proteins and viruses, can also be prepared.

In some aspects, the MIP layer is selective for a protein or polypeptide, such as a receptor-binding domain of a virus (e.g., SARS1, SARS2, SARS-CoV-2, flu or Ebola virus). In some aspects, the protein or polypeptide is a glycoprotein, such as a glycosylated spike protein. In some aspects, the glycosylated spike protein binds to an angiotensin-converting enzyme 2 (ACE2) receptor. In a particular aspect, the MIP layer is selective for the receptor binding domain of the glycosylated spike protein of SARS-CoV-2.

In some aspects, the MIP layer is selective for a virus. It will be understood that when a MIP layer is selective for a virus, such selectivity is typically mediated by a protein present on the surface of the viral particle. In a particular aspect, the protein is a viral fusion protein, such as a glycoprotein. Example viruses include, but are not limited to, Ebola, severe acute respiratory syndrome coronavirus (SARS-CoV), influenza virus (e.g., H1N1 influenza virus), Middle East respiratory syndrome coronavirus (MERS-CoV), severe acute respiratory syndrome coronavirus 2 (SARS-CoV-2), human immunodeficiency virus (HIV), Dengue virus, Chikungunya virus, hepatitis A virus, hepatitis B virus, and hepatitis C virus. In some aspects, the virus is SARS1, SARS2, SARS-CoV-2, flu or Ebola virus. In a particular aspect, the virus is SARS-CoV-2.

In some aspects, the MIP layer is selective for one or more analytes associated with a disease or condition (e.g., COVID-19), such as the glycosylated spike protein and/or RBD of SARS-CoV-2, which has been associated with COVID-19. Sensors comprising MIP layers selective for one or more disease- or condition-associated analytes (e.g., disease- or condition-associated volatile organic compounds; disease- or condition-associated proteins) can conveniently be used as diagnostic devices to detect analyte(s) associated with a particular disease or condition and thereby diagnose a subject having the disease or condition. Potential sources of analytes associated with a disease or condition include the breath (e.g., exhaled breath), sweat, blood and urine of a subject.

When an analyte is "associated with a disease or condition," the analyte has been linked to or otherwise implicated in a particular disease or condition. An analyte associated with a disease or condition can be differentially present (e.g., present in larger quantities, detectable, present) in diseased subjects or differentially absent (e.g., present in lesser quantities, undetectable, completely absent) in diseased subjects compared to their healthy counterparts. For example, certain volatile organic compounds have been shown to be differentially present in the breath of Alzheimer's disease patients as compared to their healthy counterparts. See, for example, Tisch, U., et al., "Detection of Alzheimer's and Parkinson's disease from exhaled breath using nanomaterial-based sensors," *Nanomedicine* 2013, 8(1), 43-56; and Broza, Y. Y. and Haick, H., "Nanomaterial-based sensors for detection of disease by volatile organic compound," *Nanomedicine,* 2013, 8(5), 785-806, the relevant teachings of which are incorporated herein by reference in their entireties.

In some aspects, the sensor has a thickness of about 5 millimeters or less, about 2.5 millimeters or less, or about 1 millimeter or less. In a particular aspect, the sensor has a thickness of about 1 millimeter.

In some aspects, the sensor has a length and a width, and is about 50 millimeters or less (e.g. about 5 millimeters or less) in length, and about 50 millimeters or less (e.g., about 5 millimeters or less) in width.

Suitable materials for the electrodes include, but are not limited to, gold and silver. Accordingly, in some aspects, the electrodes comprise gold. In some aspects, the electrodes comprise silver.

As further described in the Exemplification, the sensors can be used to rapidly detect one or more analytes. In some aspects, the sensor has an equilibration time of less than 60 seconds, for example, less than or about 30 seconds, less than or about 15 seconds or less than or about 10 seconds. In some additional or alternative aspects, the sensor has a response time (upon exposure to analyte) of less than 60 seconds, for example, less than or about 30 seconds, less than or about 15 seconds or less than or about 10 seconds.

As further described in the Exemplification, analyte can be removed from the sensors thereby facilitating re-use of the sensors. Thus, in some aspects, the sensor has a recovery time (e.g., to its baseline or inherent resistance upon removal of sample containing analyte) of less than 60 seconds, for example, less than or about 30 seconds, less than or about 15 seconds or less than or about 10 seconds.

The sensors and detectors described herein can be conveniently incorporated into systems for use by appropriate personnel (e.g., medical personnel, subjects suspecting they have a disease or condition intended to be diagnosed by the sensor or detector). Accordingly, also provided herein is a detector comprising a sensor described herein and a voltage source configured to apply a voltage to the MIP layer. In some aspects, the detector further comprises an ohmmeter (e.g., multimeter) in operative arrangement with the electrodes and configured to apply a voltage to the MIP layer. In some aspects, the detector further comprises a microcontroller unit capable of monitoring and transmitting data obtained from the ohmmeter (e.g., via BLUETOOTH® technology to a smart phone, for example).

Figure 1B:
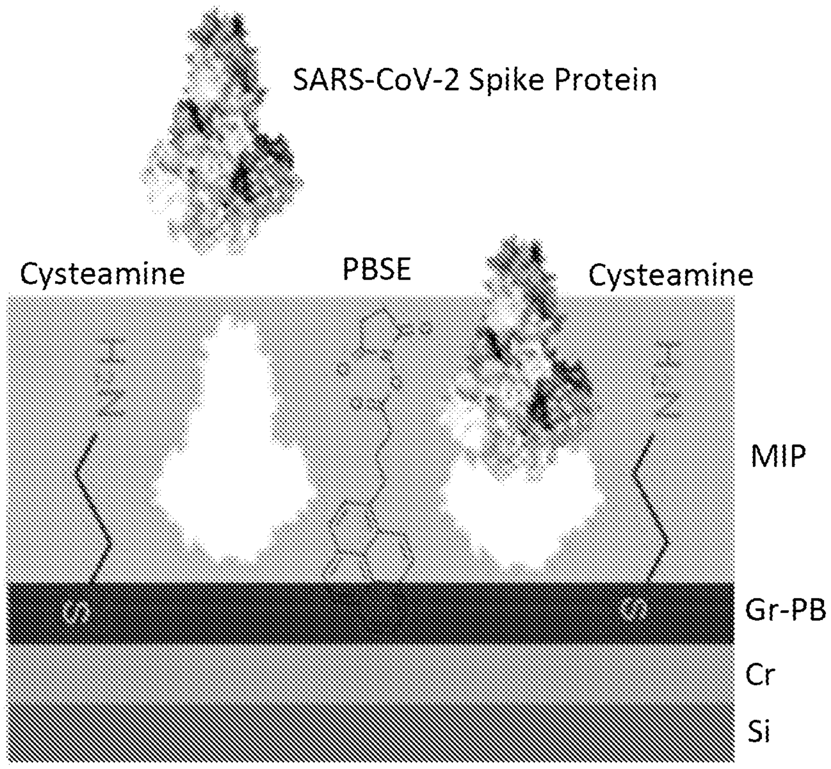
FIG. 1B is a depiction of a second-generation sensor, and shows a sensor similar to the first-generation sensor depicted in FIG. 1A, except that a graphene layer was functionalized with PBSE and cysteamine in order to attract the template molecule, with a purpose of increasing sensitivity.
Figure 1C:
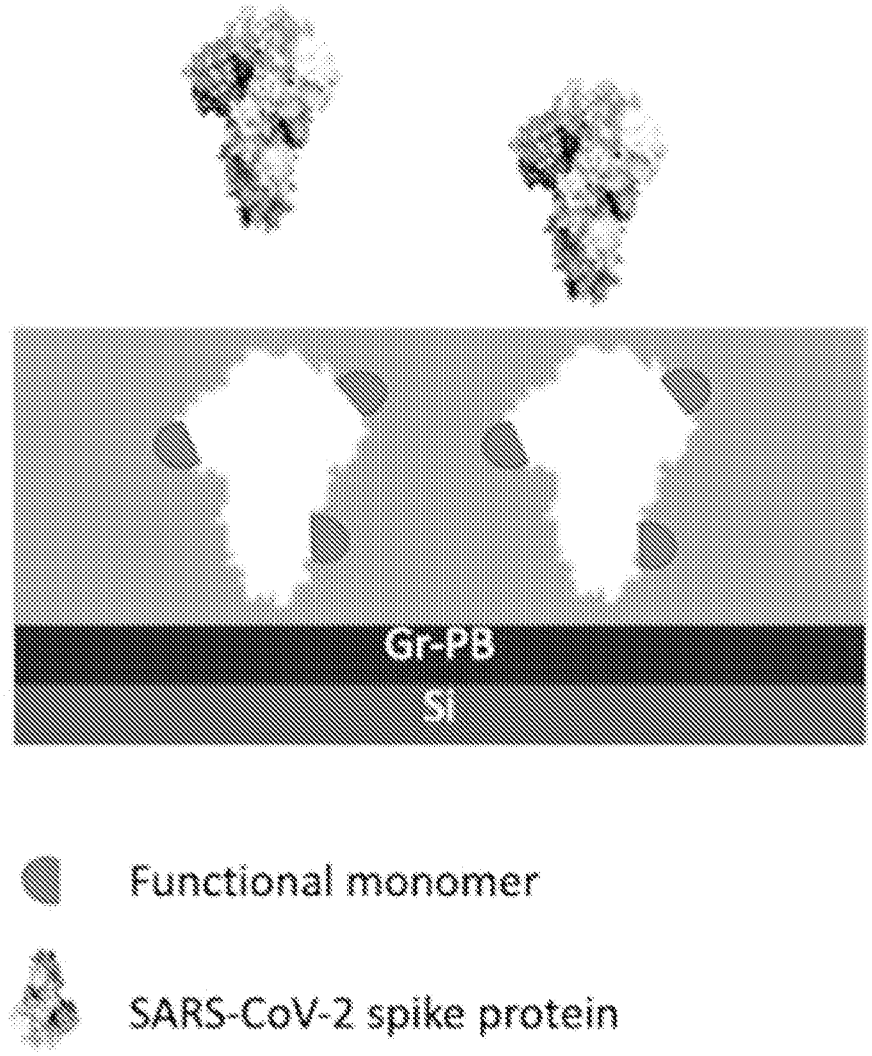
FIG. 1C is a depiction of a third-generation sensor in accordance with embodiments disclosed herein, and shows a sensor wherein functional monomers were applied and act as blocks surrounding the template molecule(s). After removal of the template molecule(s), the functional monomers stay in the polymer matrix, helping the polymer selectively bind with the template molecule. Without wishing to be bound by any particular theory, it is believed that using the functional monomer in the structure of the polymer improves selectivity of third-generation sensors.
Figure 1D:
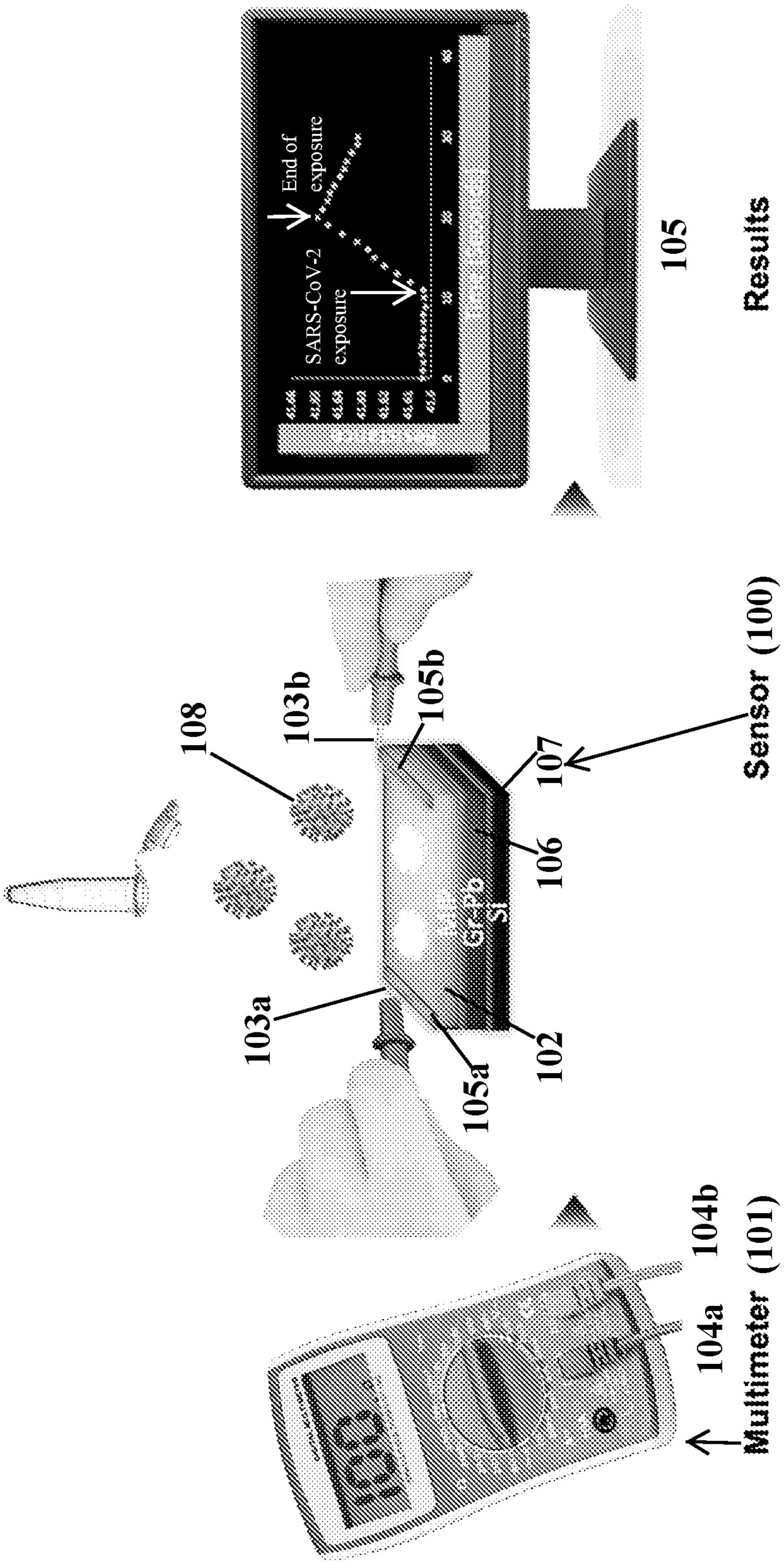
FIG. 1D is a schematic diagram, and shows use of a third-generation sensor in accordance with embodiments disclosed herein.

For example, FIG. 1D depicts incorporation of sensor 100 into a system described herein. In FIG. 1D, multimeter 101 is configured to apply a voltage to MIP layer 102 by placing probe tips 103*a*, 103*b* of probes 104*a*, 104*b* in contact with electrodes 105*a*, 105*b* of sensor 100, and by connecting probes 104*a*, 104*b* to multimeter 101 so as to complete a circuit including sensor 100 and multimeter 101. In sensor 100 depicted in FIG. 1D, electrodes 105*a*, 105*b* are on MIP layer 102, which is on graphene layer 106 comprising Prussian blue, which is on doped silicon layer 107. Typically, in use, sensor 100 is allowed to equilibrate in the absence of sample for a first period of time, and multimeter 101 is used to measure the inherent resistance of sensor 100. Sample 108 is then brought into contact with sensor 100 for a second period of time (e.g., 10 seconds), and multimeter 101 is used to measure the resistance of sensor 100. The resistance(s) measured by multimeter 101 can be transmitted to a microcontroller unit (not shown) in communication with screen 105, which can be used to visualize the resistance(s) measured.

Methods of Use

Also provided herein are methods of using the sensors described herein. One embodiment is a method of detecting an analyte in a sample (e.g., a breath, sweat, blood or urine sample, especially a breath sample, from a subject). The method comprises measuring the resistance of a sensor described herein that is in contact with the sample to obtain a measured resistance. The sensor is selective for the analyte, and the measured resistance is indicative of presence or absence of the analyte in the sample.

Another embodiment is a method of detecting a disease or condition (e.g., viral infection) in a subject. The method comprises measuring the resistance of a sensor described herein that is in contact with a sample from the subject (e.g., a breath, sweat, blood or urine sample, especially a breath sample, from a subject) to obtain a measured resistance. The sensor is selective for an analyte associated with the disease or condition (e.g., viral infection), and the measured resistance is indicative of presence or absence of the disease or condition in the subject. In some aspects, the disease or condition is a viral infection, such as COVID-19.

Yet another embodiment is a method of diagnosing a disease or condition (e.g., viral infection) in a subject (e.g., a subject suspected to have the disease or condition, or at risk for developing the disease or condition). The method comprises measuring the resistance of a sensor described herein that is in contact with a sample from the subject (e.g., a breath, sweat, blood or urine sample, especially a breath sample, from a subject) to obtain a measured resistance. The sensor is selective for an analyte associated with the disease or condition (e.g., viral infection), and the measured resistance is indicative of presence or absence of the disease or condition in the subject.

In a particular aspect, the sample comprises exhaled breath.

Analytes detectable according to the methods described herein are as described throughout this disclosure and include any of the analytes described herein, e.g., an analyte associated with a disease or condition, such as COVID-19. In some aspects, an analyte is an analyte associated with a disease or condition in a subject suspected to have the disease or condition, or at risk for developing the disease or condition.

Diseases and conditions detectable according to the methods described herein are as described throughout this disclosure and include any of the diseases and conditions described herein, e.g., COVID-19.

The sensors described herein have an inherent resistance. In the methods described herein, a difference between the inherent resistance of the sensor and the measured resistance of the sensor typically indicates presence of the analyte and, in the case of an analyte associated with a disease or condition, that the subject has the disease or condition (e.g., viral infection). In some aspects, a difference between the inherent resistance of the sensor and the measured resistance of the sensor of 5 mOhms or greater indicates presence of an analyte and, in the case of an analyte associated with a disease or condition, that the subject has the disease or condition (e.g., viral infection).

As used herein, "inherent resistance" refers to the resistance of a device described herein in the absence or substantial absence of the one or more analytes for which the device is selective. A person of ordinary skill in the art will appreciate that the methods described herein can be carried out by comparing the inherent resistance of the device (e.g., as an absolute number) to the resistance of the device contacted with a sample (e.g., also as an absolute number), such that the magnitude of the difference, if calculated, is the mathematical difference between the inherent resistance and the resistance of the device contacted with the sample. Alternatively, resistance can be based on a normalized scale, for example, using the following equation: $[(R-R_o)/R_0]\times 100$, where R is the resistance of the device contacted with a sample and $R_o$ is the inherent resistance of the device. When normalized resistance is used, the device still has an inherent resistance associated with an absolute value, but the inherent resistance is assigned a value of zero. Using this method of comparing inherent resistance and resistance of a device contacted with a sample, the change in the resistance of the device (e.g., upon exposure to a sample) is the mathematical difference between the inherent resistance of the device and the resistance of the device contacted with the sample. The methods described herein contemplate and include both methods, and either understanding of "inherent resistance."

As used herein, "subject" includes humans, domestic animals, such as laboratory animals (e.g., dogs, monkeys, pigs, rats, mice, etc.), household pets (e.g., cats, dogs, rabbits, etc.) and livestock (e.g., pigs, cattle, sheep, goats, horses, etc.), and non-domestic animals. In some aspects, the subject is a mammal. In some aspects, the subject is a human.

A person of ordinary skill in the art will be able to identify those subjects suspected to have a disease or condition detectable and/or diagnosable with a sensor described herein, for example, based on a subject's symptoms, other tests or analyses, etc. A person of ordinary skill in the art will be able to identify those subjects at risk for developing a disease or condition detectable and/or diagnosable with a sensor described herein, for example, based on exposure information, genetic information, family history or other factors known to a person of ordinary skill in the art.

In some aspects, the methods further comprise contacting the MIP layer of the sensor with the sample.

The devices described herein typically show linear behavior over the relevant range of analyte (e.g., the range of analyte expected to be present in a sample, such as a sample obtained from a subject). Accordingly, in many cases, the mathematical difference between the inherent resistance of a device described herein (however measured), and the resistance of a device contacted with a sample, can be translated into analyte quantity. In some aspects, the methods described herein further comprise calculating the amount of the analyte in the sample using the measured resistance.

In some aspects, the methods described herein further comprise providing a chamber containing the sensor and into which the subject exhales, thereby contacting the MIP layer of the sensor with the sample. In particular aspects, the chamber is sealed or substantially sealed.

The sensors and methods described herein can also be used to diagnose a disease or condition in which the analyte to be detected is differentially absent in diseased subjects compared to their healthy counterparts. Thus, in one embodiment, a method of diagnosing a disease or condition in a subject (e.g., a subject suspected to have the disease or condition, or at risk for developing the disease or condition) is provided. The method comprises measuring the resistance of a sensor described herein that has an inherent resistance, and is in contact with a sample (e.g., a breath, sweat, blood or urine sample, especially a breath sample) from the subject. Here, a lack of difference, or a difference of insufficient magnitude between the inherent resistance of the sensor and the measured resistance of the sensor indicates the subject has the disease or condition. A difference of insufficient magnitude can be assessed by comparing the difference measured to the difference expected based on a healthy subject or a population of healthy subjects, optionally taking into account any error associated with the method.

In some aspects, the methods further comprise comparing the measured resistance of a sensor according to the methods described herein, or an amount of analyte calculated from the measured resistance of a sensor according to the methods described herein to the resistance of a device contacted or in contact with a sample from a healthy subject or a population of healthy subjects or the amount of analyte in a comparable sample from a healthy subject or population of healthy subjects, respectively, or a relevant standard (e.g., a standard range) based on a healthy subject or population of healthy subjects. A difference (e.g., a clinically significant difference, a statistically significant difference, a difference taking into account any error associated with the method) between the sample and the relevant comparator indicates the subject has the disease or condition.

In some aspects, the methods further comprise comparing the resistance of a device contacted with a sample according to the methods described herein, or an amount of analyte calculated from the resistance of a device contacted with a sample according to the methods described herein to the resistance of a device contacted with a sample from a subject or a population of subjects having the disease or condition or the amount of analyte in a comparable sample from a subject or population of subjects having the disease or condition, respectively, or a relevant standard (e.g., a standard range) based on a subject or population of subjects having the disease or condition. A lack of difference (e.g., a difference of insufficient magnitude, optionally taking into account any error associated with the method; a clinically insignificant difference, a statistically insignificant difference) between the sample and the relevant comparator indicates the subject has the disease or condition.

In some aspects, measuring the resistance comprises allowing the sensor to equilibrate in the absence of the sample for a first period of time (e.g., an equilibration time), and recording a signal indicative of an inherent resistance, and bringing the sensor and the sample into contact with one another for a second period of time (e.g., a response time), and recording a signal indicative of the measured resistance. In some aspects, the first period of time (e.g., an equilibration time) and the second period of time (e.g., response time) are each independently less than 60 seconds, for example, less than or about 30 seconds, less than 30 seconds, less than or about 15 seconds, less than 15 seconds, less than or about 10 seconds or less than 10 seconds.

In some aspects, measuring the resistance further comprises bringing the sensor and the sample out of contact with one another, and allowing the sensor to recover for a third period of time (e.g., a recovery time). In some aspects, the third period of time (e.g., recovery time) is less than 60 seconds, for example, less than or about 30 seconds, less than 30 seconds, less than or about 15 seconds, less than 15 seconds, less than or about 10 seconds or less than 10 seconds.

In some aspects, the first, second and third periods of time are each about 10 seconds.

Methods of Making

Also provided herein are methods of fabricating a sensor. In one embodiment, the method comprises forming a graphene layer on a doped silicon layer, and forming a MIP layer derived from a MW monomer and functional monomer on the graphene layer.

In some aspects, the method further comprises etching a surface of the doped silicon layer, and forming the graphene layer on the etched surface of the doped silicon layer.

In some aspects, forming the MIP layer comprises incubating the functional monomer with a template molecule under conditions suitable to establish an interaction between the functional monomer and the template molecule, thereby forming a pre-polymerization complex; and polymerizing the pre-polymerization complex and the MIP monomer, thereby forming the MIP layer. In some aspects, forming the MIP layer further comprises removing the template molecule from the MIP layer.

In some aspects, the MIP layer is derived from a MIP monomer, functional monomer and cross-linking monomer, and forming the MIP layer comprises incubating the functional monomer with a template molecule under conditions suitable to establish an interaction between the functional monomer and the template molecule, thereby forming a pre-polymerization complex; and polymerizing the pre-polymerization complex, the MW monomer and the cross-linking monomer, thereby forming the MIP layer. In some aspects, forming the MIP layer further comprises removing the template molecule from the MIP layer.

In some aspects, the method of making further comprises applying electrodes to the sensor such that the electrodes are in operative arrangement with the MIP layer and configured to provide a signal indicative of a resistance. In some aspects, the electrodes are applied to the MIP layer. Electrodes are as described herein.

Molecularly imprinted polymers, graphene layers and other variations on the sensor are as described herein.

Exemplification

Abstract. A third-generation of electrochemical gas sensors to detect SARS-CoV-2 in the air were fabricated and tested. The advantages of the third-generation sensors compared to the previous generations are improved consistency, repeatability, and selectivity. All the sensors were tested against bovine serum albumin (BSA), water, phosphate buffer solution (PBS), the Middle East respiratory syndrome (MERS), severe acute respiratory syndrome (SARS), Ebola, and flu virus. In the tests, the new generation of sensors was highly selective, particularly as compared to the previous generations of sensors. The first- and third-generation sensors were also blind tested with an 86-sample kit. The first-generation sensor was 37.5% selective and 61% sensitive against the kit, while the third-generation sensor was 75% selective and 80% sensitive against the kit. The process of fabricating the sensors is repeatable, as we made at least 20 sensors of this kind have been made.

Introduction. Three generations of electrochemical gas sensors are depicted in FIGS. 1A-1C, and described below.

The first generation of molecularly-imprinted polymer (MIP) sensors were polymerized around a template molecule by placing the template molecule in a polymer matrix. In the first-generation sensors, the cavities so produced ended up being larger than and with a slightly different shape from the template molecule. A first-generation sensor is depicted in FIG. 1A. First-generation-type sensors are also disclosed in U.S. Patent Appln. Publication No. US 2019/0313944, the entire contents of which are incorporated herein by reference.

The second generation of these sensors were functionalized sensors. In order to enhance the sensitivity of the sensor up to 80,000 times, a graphene layer was functionalized with PBSE and cysteamine to help the sensor attract the virus. The structure of the sensor and the MIP fabrication step were unchanged in the second-generation sensors. A second-generation sensor is depicted in FIG. 1B. Second-generation-type sensors are also disclosed in International Application No. PCT/US2021/014248, the entire contents of which are incorporated herein by reference.

The third generation of the MIP sensors were fabricated with an aim of detecting the template molecule selectively with the help of functional monomers. Functional monomers act as blocks around the template molecule that help for the orientation of the detecting template molecule. Using functional monomers improves the selectivity of the sensors. The selective recognition abilities of the imprinted polymers are believed to be due to the formation of a complex between a target analyte and the selected functional monomer(s) during a pre-polymerization step. The choice of the monomer(s) represents a useful point in the preparation of effective MIPs and is based on the ability of the monomer(s) to establish interactions with the functional groups of the template molecule in a covalent or non-covalent way.

Dopamine (DA) and methacrylic acid (MAA) were used as two functional monomers. Chromium was not used in the structure of these sensors. Instead, a highly doped silicon was used and etched with hydrofluoric acid (HF) in order to remove silicon oxide completely. Removing chromium from the structure of the sensor helped adhesion of graphene with a silicon substrate and decreased a Schottky barrier height that forms in a metal-semiconductor junction. Replacing a metal-semiconductor junction with a semiconductor-semiconductor junction lowered the Schottky barrier height from almost 1.5 to 0.5 eV [1]. A third-generation sensor is depicted in FIG. 1C.

Fabrication. Two example functional monomers were chosen based on their structure and their ability to bind with the template molecule. Dopamine and methacrylic acid are both much smaller than the template molecule and have functions to bind with the template molecule immediately. Proper solvents needed to be used in order to remove the template molecule from the polymer matrix but not the functional monomer. Example fabrication steps of the sensors with these functional monomers are as follows:

Dopamine (DA) was used as a functional monomer for fabricating a MIP sensor to detect bovine hemoglobin [2]. Dopamine was discovered to self-polymerize within a weak alkaline aqueous solution into thin adherent polydopamine (PDA) films, which may be coated on various inorganic and organic substrates. Dopamine hydrochloride was purchased from Sigma Aldrich. After the deposition of graphene and Prussian-blue on a surface of etched silicon substrate, the surface was polymerized with a complex formed from a mixture of the template molecule and the functional monomer. The complex solution was made with 100 μl of the template protein solution containing 30 μg of the protein (full-length spike protein (G614 sensor) or RBD s-protein (RBD sensor)) mixed with 1 mg of dopamine hydrochloride, sonicated for 10 minutes, and added to the electrolyte containing 200 ml of phosphate buffer solution and 1.38 ml of pyrrole (pH 6.8). Later, the electrolyte was used to polymerize the surface of the sensor. The sensor was then washed with hydrochloric acid solution (1 mol/L, 2 mL) and methanol (8 mL).

Methacrylic acid (MAA) was applied as a functional monomer in a sensor structure to detect many proteins and materials [3,4]. Ethylene glycol dimethacrylate (EGDMA) is often used with MAA as a cross-linker. MAA and EGDMA were purchased from Sigma Aldrich. After deposition of the graphene and Prussian-blue on the surface of etched silicon substrate, the surface was polymerized with a complex formed from the mixture of the template molecule and the functional monomer. The complex was formed through mixing of 200 μl of the template protein solution (containing 60 μg of the template protein) along with 90 μl of methanol and acetonitrile (volume 1:1) and 0.51 μl of MAA. The mixture was sonicated for 10 minutes. 1.41 μl of EGDMA was then added to the mixture, and the resulting mixture was sonicated for another 10 minutes. The mixture was then added to the MW electrolyte solution containing 200 ml of phosphate buffer solution and 1.38 ml of pyrrole (pH 6.8) for polymerization.

Testing Results. To compare the functionality of each generation of the sensors, the generations were tested against a SARS-CoV-2 gamma-inactivated virus and a SARS-CoV-2 spike protein for sensitivity measurements. For the selectivity measurements, the sensors were tested against bovine serum albumin (BSA), water, phosphate buffer solution (PBS), Middle East respiratory syndrome (MERS), severe acute respiratory syndrome (SARS), Ebola, and flu virus.

Figure 2A:
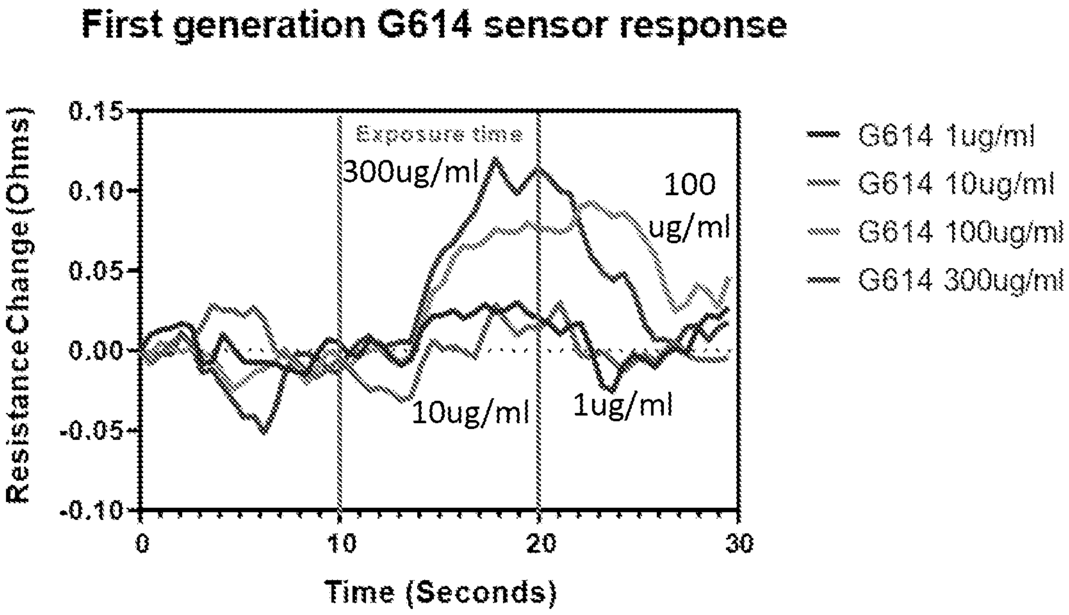
FIG. 2A is a graph of resistance change versus time, and shows the resistance change of a first-generation G614 sensor exposed to G614 SARS-CoV-2 spike protein.
Figure 2B:
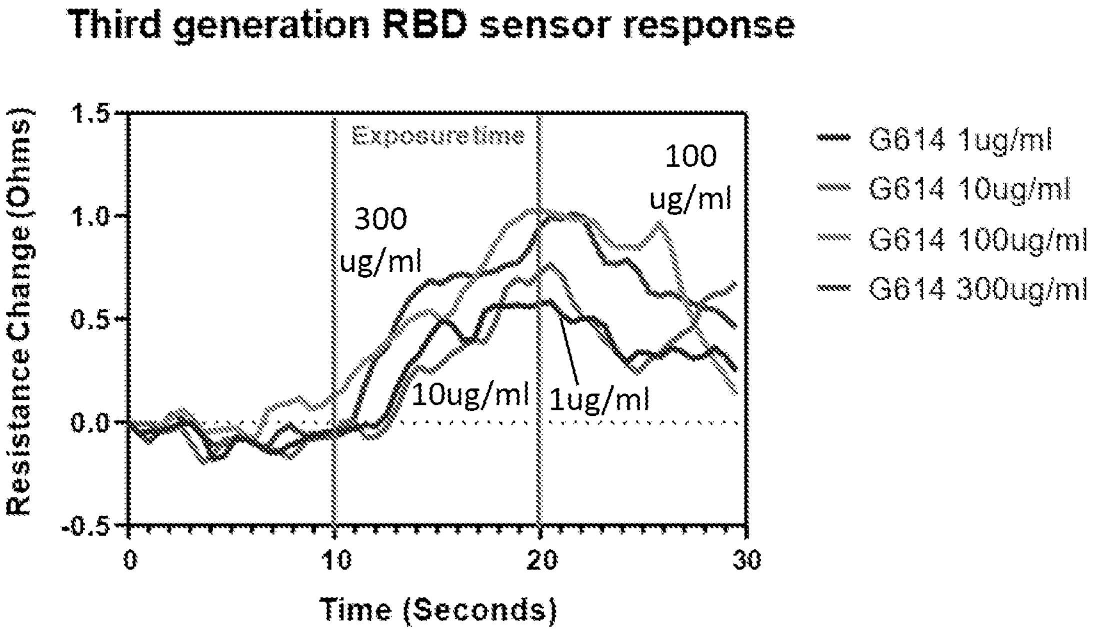
FIG. 2B is a graph of resistance change versus time, and shows the resistance change of a third-generation receptor binding domain (RBD) sensor exposed to G614 SARS-CoV-2 spike protein.
Figure 3A:
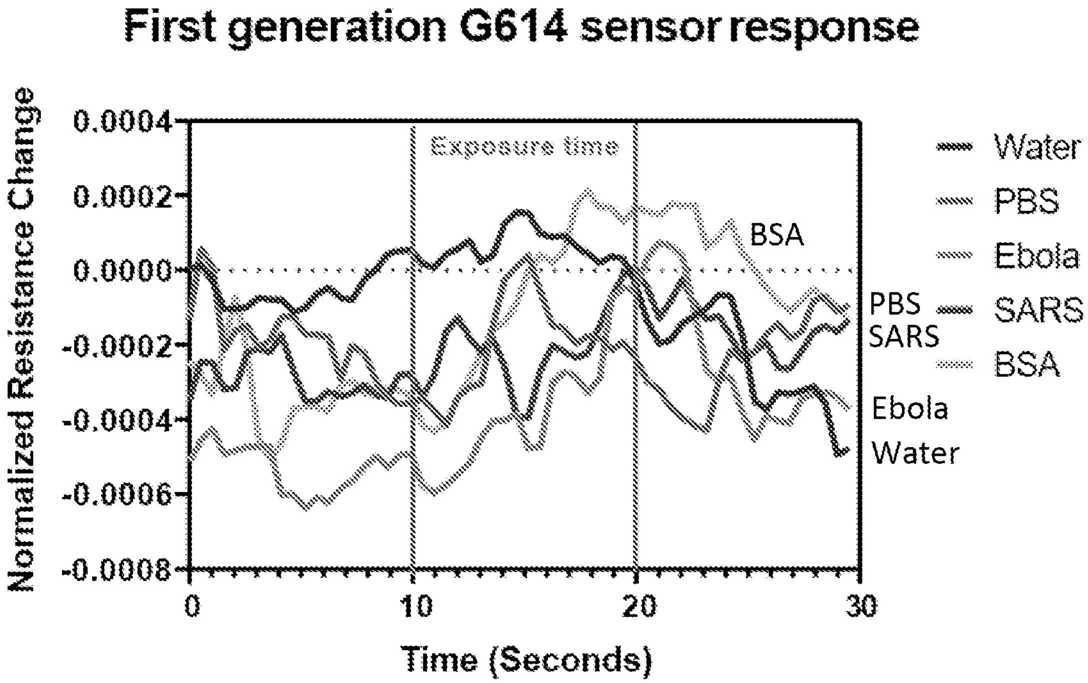
FIG. 3A is a graph of normalized resistance change versus time, and shows the selectivity of a first-generation G614 sensor exposed to the indicated agents.
Figure 3B:
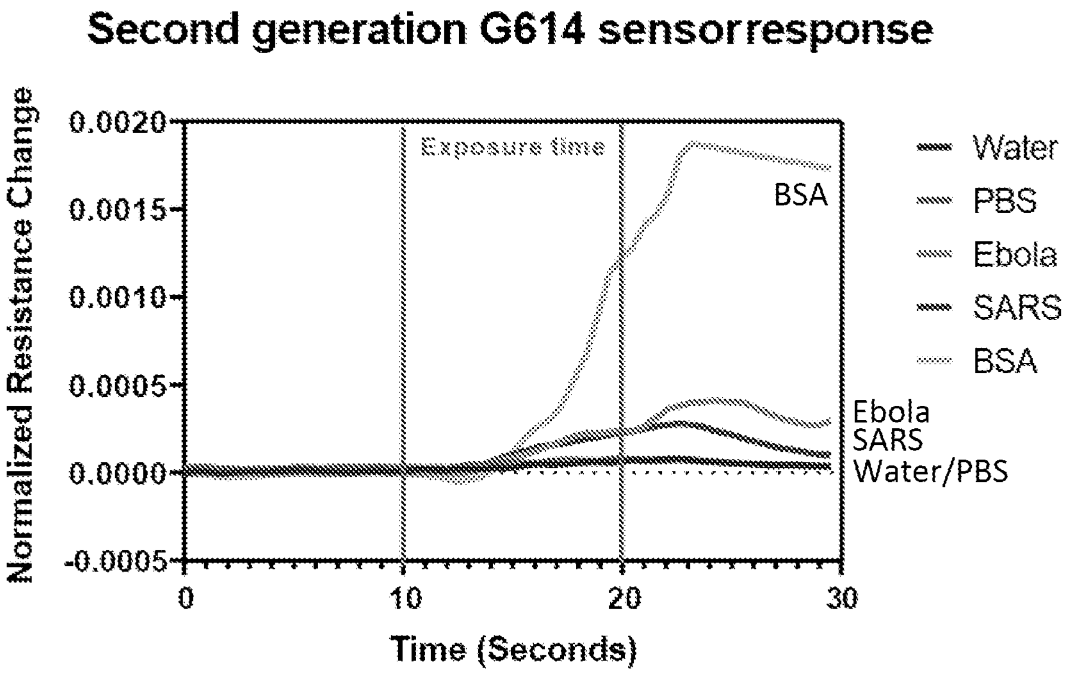
FIG. 3B is a graph of normalized resistance change versus time, and shows the selectivity of a second-generation G614 sensor exposed to the indicated agents.
Figure 3C:
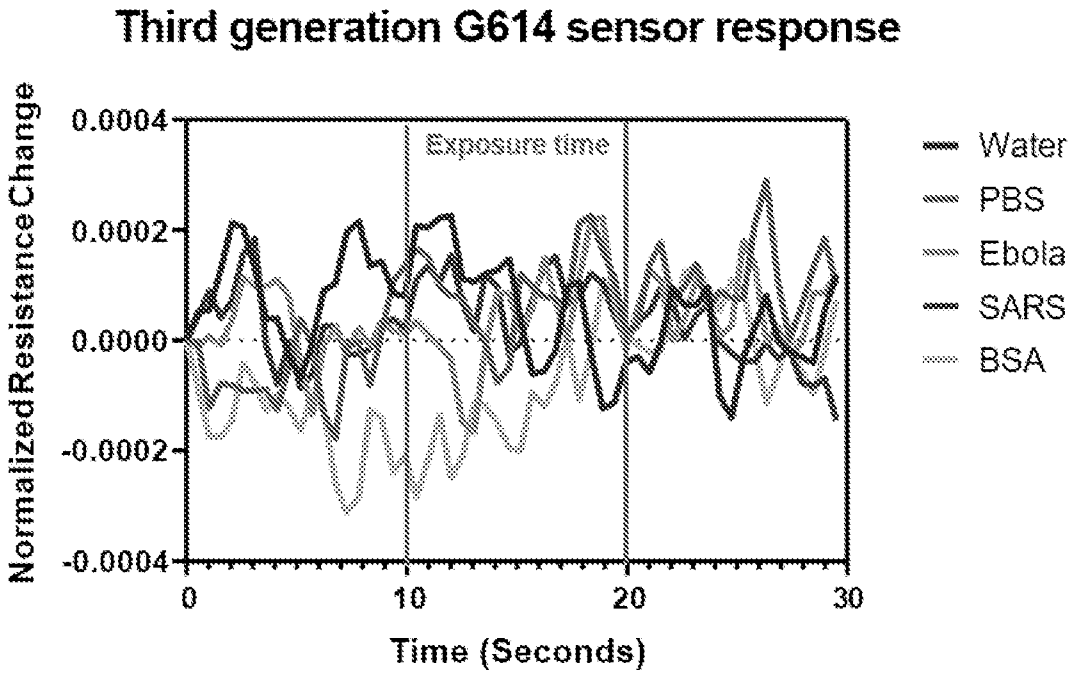
FIG. 3C is a graph of normalized resistance change versus time, and shows the selectivity of a third-generation G614 sensor exposed to the indicated agents.
Figure 3D:
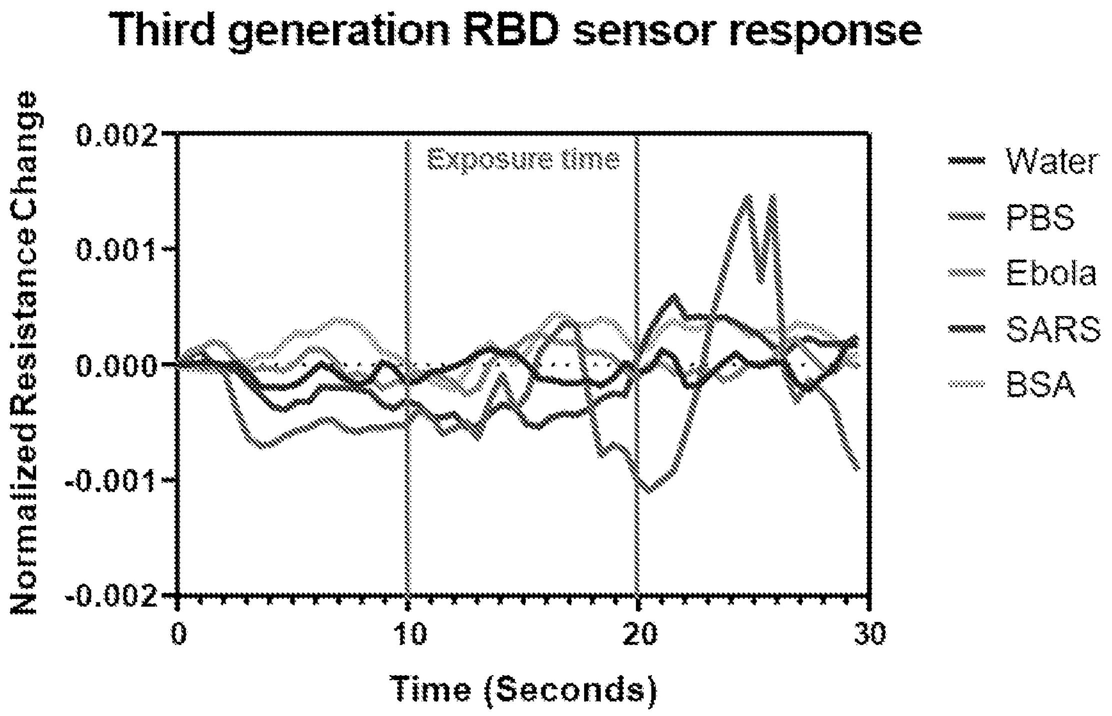
FIG. 3D is a graph of normalized resistance change versus time, and shows the selectivity of a third-generation RBD sensor exposed to the indicated agents.

Sensitivity. The first-generation and the third-generation sensors were tested with different concentrations of a SARS-CoV-2 spike protein, the G614 mutation. FIGS. 2A and 2B show that, while the third-generation sensor clearly detected all the concentrations of G614 spike protein from 1 to 300 μg/ml, the first-generation sensor could not detect the lower concentrations (1-10 μg/ml). Although the initial purpose of adding the functional monomers to the polymer matrix was for increasing the selectivity, it is clear that having blocks around the template molecule increased the sensitivity as well. The sensors were exposed to the G614 spike protein for 10 seconds from seconds 10-20. The first 10 seconds were for the sensor to stabilize, and the last 10 seconds were for the sensor to return to its baseline resistance.

Selectivity. A first-generation G614 sensor, a second-generation G614 sensor, a-third generation G614 sensor, and a third-generation RBD sensor were tested with water, PBS, Ebola, SARS, and BSA. The sensors were exposed for 10 seconds (from seconds 10-20). The first 10 seconds were for the sensor to stabilize, and the last 10 seconds were for the sensor to return to its baseline resistance. The results of the testing are graphed in FIGS. 3A-3D. It turned out that the first-generation sensor exhibited a false positive with Ebola and BSA, and the second-generation sensor falsely detected Ebola, SARS and BSA. The third-generation G614 sensor had a false positive with BSA. However, the third-generation RBD sensor did not falsely detect any of the samples.

Figure 4A:
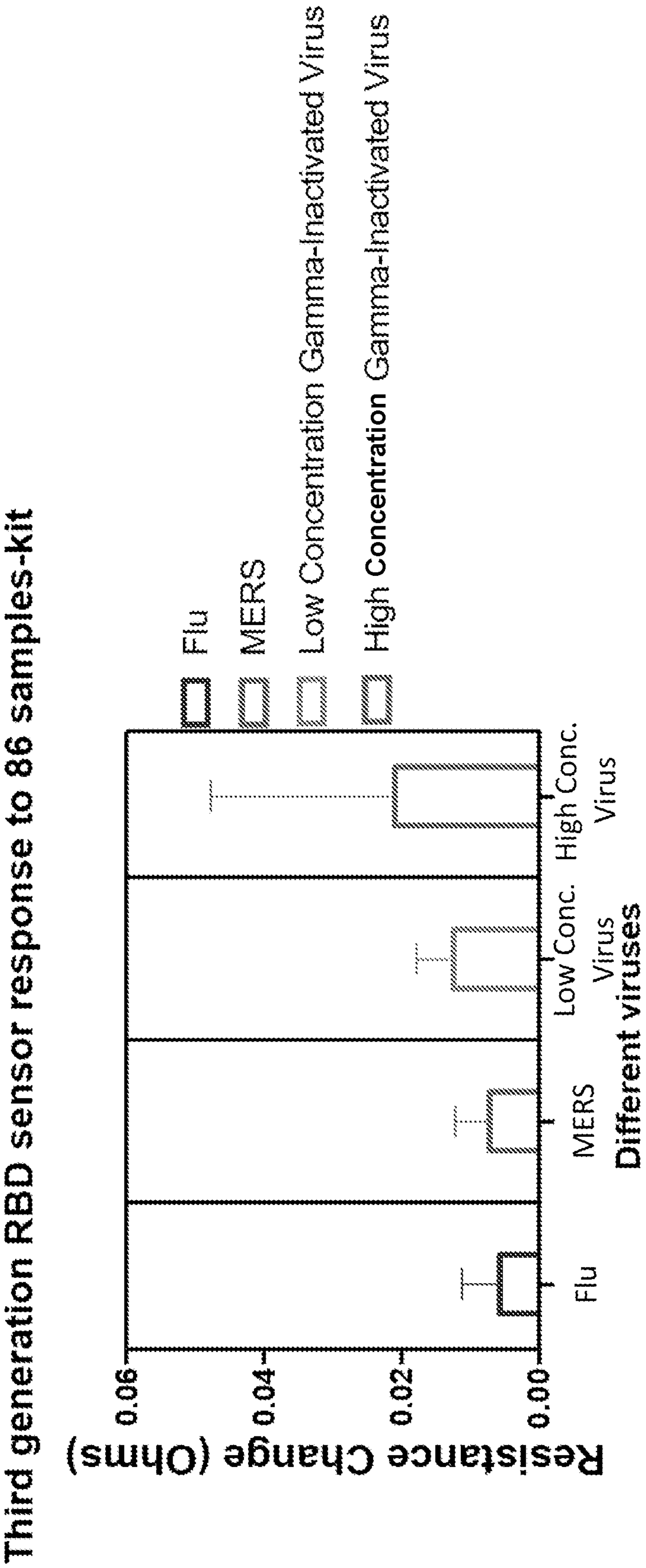
FIG. 4A shows the response of a third-generation RBD sensor to an 86-sample kit.
Figure 4B:
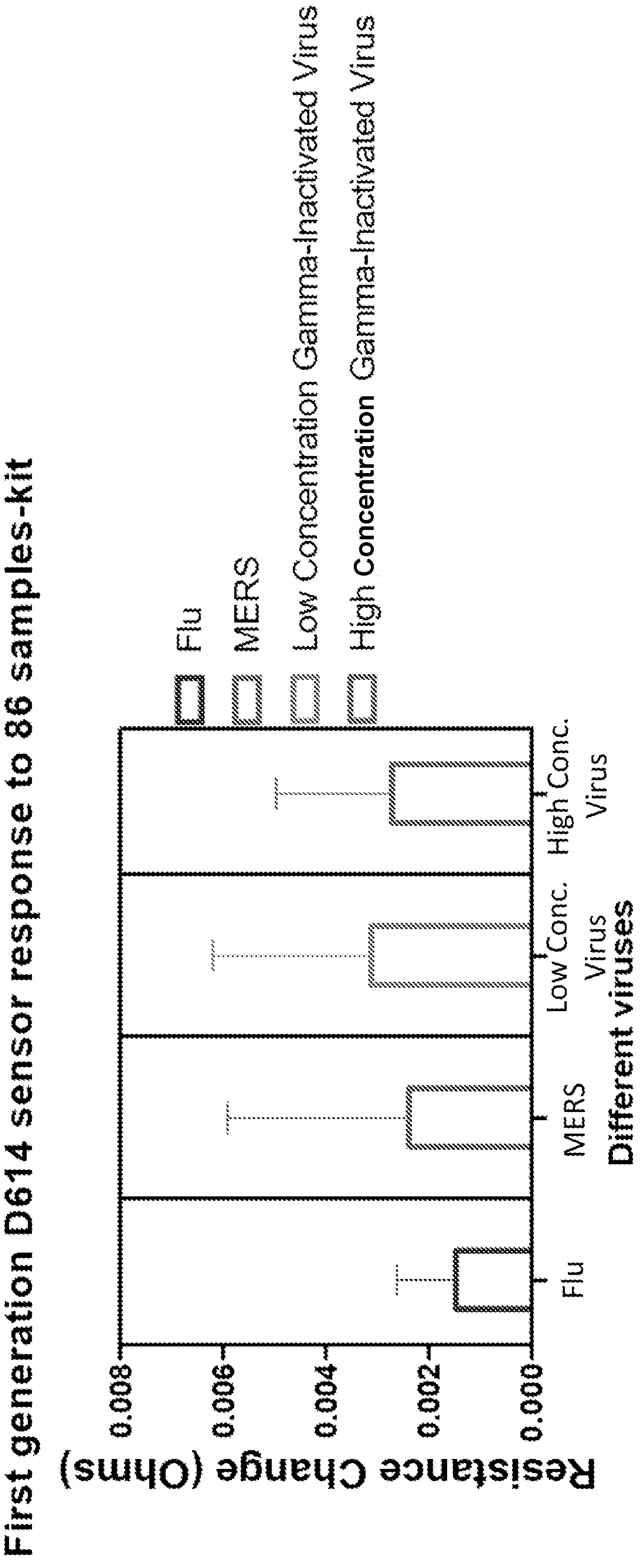
FIG. 4B shows the response of a first-generation G614 sensor to an 86-sample kit.

In another comprehensive experiment, the sensors were tested with 86-sample kits containing 8 flu virus samples, 2 MERS virus samples, 33 high concentration samples containing gamma-inactivated SARS-CoV-2 virus at concentrations above 1,000 copies/ml, and 36 low concentration samples containing gamma-inactivated SARS-CoV-2 virus at concentrations below 500 copies/ml. FIGS. 4A and 4B show that the first-generation D614 sensor was 37.5% selective and 61% sensitive against the kit (FIG. 4B), while the third-generation RBD sensor was 75% selective and 80% sensitive against the kit (FIG. 4A).

Conclusions. The third generation of the electrochemical gas sensors to detect SARS-CoV-2 in the air were introduced, fabricated and tested. All the sensors were tested against SARS-CoV-2 gamma-inactivated virus and SARS-CoV-2 spike protein for sensitivity. While the third-generation sensor could detect all the lower concentrations of virus, the first-generation sensor only detected the higher concentrations of virus. The sensors were also tested with bovine serum albumin (BSA), water, phosphate buffer (PBS) solution, Middle East respiratory syndrome (MERS), severe acute respiratory syndrome (SARS), Ebola, and flu virus for selectivity. The third-generation sensors are highly selective compared to the previous generations of sensors. These sensors are consistent and repeatable, as 20 of them were fabricated and tested and showed all similar behaviors.

REFERENCES

1. Liu F, Kar S, Quantum carrier reinvestment-induced ultrahigh and broadband photocurrent response in Graphene-Silicon Junctions, ACS Nanp 8, 2014, 10270-10279.
2. Luo J, Jiang S, Liu X, Electrochemical sensor for bovine hemoglobin based on a novel graphene-molecular imprinted polymers composite as recognition element, Sensors and Actuators B 203 (2014) 782-789.
3. Parisi O I, Dattilo M, Patitucci F, Malivindi R, Pezzi V, Perrotta I, Ruffo M, Amone F, PuociF, Monoclonal-type plastic antibodies for SARS-CoV-2 based on Molecularly Imprinted Polymers, https://doi.org/10.1101/2020.05.28.120709 doi:bioRxiv preprint.
4. Kong, Y, Wang N, Ni X, Yu Q, Liu H, Huang W, Xu W, Molecular dynamics simulations of molecularly imprinted polymer approaches to the preparation of selective materials to remove norfloxacin, J of Applied Polymer, 2016, 1-11.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments contemplated herein.

What is claimed is:

1. A sensor, comprising:
a doped silicon layer having an etched surface;
a graphene layer directly on the etched surface of the doped silicon layer;
a molecularly imprinted polymer (MIP) layer derived from a MIP monomer and functional monomer, the MIP layer disposed on the graphene layer; and
electrodes in operative arrangement with the MIP layer, and said electrodes configured to provide a signal indicative of a resistance of the sensor.

2. The sensor of claim 1, wherein the graphene layer comprises graphene and potassium ferrocyanide.

3. The sensor of claim 1, wherein the MIP monomer is pyrrole.

4. The sensor of claim 1, wherein the functional monomer is methacrylic acid or dopamine, or a salt thereof, or a combination of any of the foregoing.

5. The sensor of claim 1, wherein the MIP layer is further derived from a cross-linking monomer.

6. The sensor of claim 5, wherein the cross-linking monomer is ethylene glycol dimethacrylate (EGDMA).

7. The sensor of claim 1, wherein:
the graphene layer directly on the etched surface comprises graphene and potassium ferrocyanide; and
the MIP layer comprises poly(pyrrole-co-EGDMA-co-methacrylic acid) or poly(pyrrole-co-dopamine).

8. The sensor of claim 1, wherein the MIP layer is selective for one or more analytes.

9. The sensor of claim 8, wherein the one or more analytes is in gas or aerosol form.

10. The sensor of claim 8, wherein the one or more analytes is a receptor-binding domain of a virus.

11. The sensor of claim 8, wherein the one or more analytes is a glycoprotein.

12. The sensor of claim 11, wherein the glycoprotein is a glycosylated spike protein.

13. The sensor of claim 10, wherein the virus is SARS-COV-2.

14. The sensor of claim 8, wherein the one or more analytes is SARS-CoV-2.

15. The sensor of claim 8, wherein the one or more analytes is associated with COVID-19.

16. A detector comprising:
a sensor of claim 1; and
a voltage source configured to apply a voltage to the MIP layer.

17. The detector of claim 16, further comprising an ohmmeter in operative arrangement with the electrodes and configured to output a measurement of the resistance.

18. A method of detecting an analyte in a sample, comprising:

measuring the resistance of a sensor of claim 1 that is in contact with the sample to obtain a measured resistance, wherein:

the sensor is selective for the analyte; and the measured resistance is indicative of presence or absence of the analyte in the sample.

19. A method of detecting a viral infection in a subject, comprising:

measuring the resistance of a sensor of claim 1 that is in contact with a sample from a subject to obtain a measured resistance, wherein:

the sensor is selective for an analyte associated with the viral infection; and the measured resistance is indicative of presence or absence of the viral infection in the subject.

20. A method of fabricating a sensor, comprising:

etching a surface of a doped silicon layer;

forming a graphene layer directly on the etched surface of the doped silicon layer; and forming a MIP layer derived from a MIP monomer and functional monomer on the graphene layer, comprising the steps of:

incubating the functional monomer with a template molecule under conditions suitable to establish an interaction between the functional monomer and the template molecule, thereby forming a pre-polymerization complex;

polymerizing the pre-polymerization complex and the MIP monomer; and removing the template molecule from the MIP layer.

21. The sensor of claim 1, wherein the doped silicon layer has a doping level greater than $10^{20}$ $m^{-3}$.

* * * * *